United States Patent
Mower et al.

(10) Patent No.: US 12,274,634 B2
(45) Date of Patent: Apr. 15, 2025

(54) PLIANT MEMBERS FOR RECEIVING AND AIDING IN THE DEPLOYMENT OF VASCULAR PROSTHESES

(71) Applicant: Merit Medical Systems, Inc., South Jordan, UT (US)

(72) Inventors: Wayne Mower, Bountiful, UT (US); Michael Adams, Bluffdale, UT (US); Zeke Eller, Plano, TX (US); John Hall, North Salt Lake, UT (US); Christopher Cindrich, Highland, UT (US)

(73) Assignee: Merit Medical Systems, Inc., South Jordan, UT (US)

(*) Notice: Subject to any disclaimer, the term of this patent is extended or adjusted under 35 U.S.C. 154(b) by 950 days.

(21) Appl. No.: 17/068,521

(22) Filed: Oct. 12, 2020

(65) Prior Publication Data
US 2021/0161692 A1    Jun. 3, 2021

Related U.S. Application Data

(63) Continuation of application No. 15/718,419, filed on Sep. 28, 2017, now Pat. No. 10,799,378.
(Continued)

(51) Int. Cl.
*A61F 2/966* (2013.01)
*A61B 17/00* (2006.01)
(Continued)

(52) U.S. Cl.
CPC .............. *A61F 2/966* (2013.01); *A61B 17/00* (2013.01); *A61B 2017/00407* (2013.01);
(Continued)

(58) Field of Classification Search
CPC .......... A61B 17/00; A61B 2017/00407; A61F 2/966; A61F 2/82; A61F 2/9517; A61F 2002/9665
See application file for complete search history.

(56) References Cited

U.S. PATENT DOCUMENTS 3,115,138 A    12/1963    McElvenny et al.
3,875,941 A    4/1975    Adair
(Continued)

FOREIGN PATENT DOCUMENTS

CN    210185778    3/2020
DE    9209908 U1    9/1992
(Continued)

OTHER PUBLICATIONS

European Examination Report dated Apr. 26, 2021 for EP11846358.7.
(Continued)

*Primary Examiner* — Sarah A Long
(74) *Attorney, Agent, or Firm* — Dorsey & Whitney LLP

(57) ABSTRACT

A vascular prosthesis deployment device and related methods are disclosed. In some embodiments the deployment device may include a delivery catheter assembly. The delivery catheter assembly may include a pliant member, wherein the pliant member is configured receive a vascular prosthesis. The pliant member may also be configured to aid in incrementally deploying a vascular prosthesis.

20 Claims, 22 Drawing Sheets

Related U.S. Application Data

(60) Provisional application No. 62/401,628, filed on Sep. 29, 2016.

(51) Int. Cl.

| | |
|---|---|
| *A61F 2/82* | (2013.01) |
| *A61F 2/95* | (2013.01) |
| *A61M 25/00* | (2006.01) |

(52) U.S. Cl.
CPC .............. *A61F 2/82* (2013.01); *A61F 2/9517* (2020.05); *A61F 2002/9665* (2013.01); *A61M 25/0009* (2013.01); *A61M 25/0026* (2013.01); *A61M 2025/0034* (2013.01); *A61M 2025/0039* (2013.01); *A61M 2205/0216* (2013.01)

(56) References Cited

U.S. PATENT DOCUMENTS

| | | | |
|---|---|---|---|
| 3,991,763 | A | 11/1976 | Genese |
| 4,029,095 | A | 6/1977 | Pena |
| 4,122,851 | A | 10/1978 | Grossner |
| 4,139,130 | A | 2/1979 | Glusker et al. |
| 4,265,381 | A | 5/1981 | Muscatell |
| 4,429,693 | A | 2/1984 | Blake et al. |
| 4,435,171 | A | 3/1984 | Goldberg et al. |
| 4,511,358 | A | 4/1985 | Johnson, Jr. et al. |
| 4,529,402 | A | 7/1985 | Weilbacher et al. |
| 4,569,674 | A | 2/1986 | Phillips et al. |
| 4,582,508 | A | 4/1986 | Pavelka |
| 4,583,972 | A | 4/1986 | Hunter, III et al. |
| 4,642,088 | A | 2/1987 | Gunter |
| 4,666,432 | A | 5/1987 | McNeish et al. |
| 4,850,955 | A | 7/1989 | Newkirk |
| 4,904,245 | A | 2/1990 | Chen et al. |
| 4,913,141 | A | 4/1990 | Hillstead |
| 4,981,474 | A | 1/1991 | Bopp et al. |
| 5,019,059 | A | 5/1991 | Goldberg et al. |
| 5,067,950 | A | 11/1991 | Broadnax, Jr. |
| 5,087,251 | A | 2/1992 | Heyman et al. |
| 5,201,757 | A | 4/1993 | Heyn et al. |
| 5,313,938 | A | 5/1994 | Garfield et al. |
| 5,413,575 | A | 5/1995 | Haenggi |
| 5,425,719 | A | 6/1995 | Lessing, Jr. |
| 5,472,325 | A | 12/1995 | Svendsen |
| 5,496,299 | A | 3/1996 | Felix et al. |
| 5,534,007 | A | 7/1996 | Germain et al. |
| 5,591,172 | A | 1/1997 | Bachmann et al. |
| 5,591,196 | A | 1/1997 | Marin et al. |
| 5,603,698 | A | 2/1997 | Roberts et al. |
| 5,645,559 | A | 7/1997 | Hachtman et al. |
| 5,733,325 | A | 3/1998 | Robinson et al. |
| 5,735,301 | A | 4/1998 | Rower |
| 5,755,769 | A | 5/1998 | Richard et al. |
| 5,759,186 | A | 6/1998 | Bachmann et al. |
| 5,824,041 | A | 10/1998 | Lenker et al. |
| 5,868,755 | A | 2/1999 | Kanner et al. |
| 5,876,448 | A | 3/1999 | Thompson et al. |
| 5,916,147 | A | 6/1999 | Boury |
| 5,944,727 | A | 8/1999 | Ahari et al. |
| 5,968,052 | A | 10/1999 | Sullivan, III et al. |
| 5,980,499 | A | 11/1999 | Ekey |
| 6,015,429 | A | 1/2000 | Lau et al. |
| 6,093,194 | A | 7/2000 | Mikus et al. |
| 6,099,511 | A | 8/2000 | Devos et al. |
| 6,123,715 | A | 9/2000 | Amplatz |
| 6,143,021 | A | 11/2000 | Staehle |
| 6,146,415 | A | 11/2000 | Fitz |
| 6,162,231 | A | 12/2000 | Mikus et al. |
| 6,241,757 | B1 | 6/2001 | An et al. |
| 6,261,276 | B1 | 7/2001 | Reitsma |
| 6,270,524 | B1 | 8/2001 | Kim |
| 6,283,992 | B1 | 9/2001 | Hankh et al. |
| 6,368,339 | B1 | 4/2002 | Amplatz |
| 6,383,211 | B1 | 5/2002 | Staehle |
| 6,391,051 | B2 | 5/2002 | Sullivan, III et al. |
| 6,413,269 | B1 | 7/2002 | Bui et al. |
| 6,416,545 | B1 | 7/2002 | Mikus et al. |
| 6,428,566 | B1 | 8/2002 | Holt |
| 6,443,980 | B1 | 9/2002 | Wang et al. |
| 6,447,531 | B1 | 9/2002 | Amplatz |
| 6,461,319 | B1 | 10/2002 | Ekey |
| 6,514,261 | B1 | 2/2003 | Randall et al. |
| 6,520,983 | B1 | 2/2003 | Colgan et al. |
| 6,530,933 | B1 | 3/2003 | Yeung et al. |
| 6,574,800 | B1 | 6/2003 | Leger et al. |
| 6,599,296 | B1 | 7/2003 | Gillick et al. |
| 6,599,308 | B2 | 7/2003 | Amplatz |
| 6,610,032 | B1 | 8/2003 | Prody |
| 6,613,079 | B1 | 9/2003 | Wolinsky et al. |
| 6,616,675 | B1 | 9/2003 | Evard et al. |
| 6,620,132 | B1 | 9/2003 | Skow |
| 6,629,981 | B2 | 10/2003 | Dennis et al. |
| 6,645,143 | B2 | 11/2003 | Vantassel et al. |
| 6,669,719 | B2 | 12/2003 | Wallace et al. |
| 6,726,712 | B1 | 4/2004 | Raeder-Devens et al. |
| 6,740,068 | B1 | 5/2004 | Aruffo et al. |
| 6,746,480 | B2 | 6/2004 | Scholz et al. |
| 6,770,101 | B2 | 8/2004 | Desmond, III et al. |
| 6,776,791 | B1 | 8/2004 | Jody et al. |
| 6,821,295 | B1 | 11/2004 | Farrar |
| 6,866,669 | B2 | 3/2005 | Buzzard et al. |
| 6,887,223 | B2 | 5/2005 | Bisbee |
| 6,893,413 | B2 | 5/2005 | Martin |
| 6,926,732 | B2 | 8/2005 | Derus et al. |
| 6,955,685 | B2 | 10/2005 | Escamilla et al. |
| 7,004,966 | B2 | 2/2006 | Edwin et al. |
| 7,083,640 | B2 | 8/2006 | Lombardi et al. |
| 7,309,350 | B2 | 12/2007 | Landreville et al. |
| 7,309,351 | B2 | 12/2007 | Escamilla et al. |
| 7,335,224 | B2 | 2/2008 | Ohlenschaeger |
| 7,393,357 | B2 | 7/2008 | Stelter et al. |
| 7,473,271 | B2 | 1/2009 | Gunderson |
| 7,591,848 | B2 | 9/2009 | Allen |
| 7,637,942 | B2 | 12/2009 | Mangiardi et al. |
| 7,661,152 | B2 | 2/2010 | Manzano-Rivera |
| 7,731,654 | B2 | 6/2010 | Mangiardi et al. |
| 7,766,886 | B2 | 8/2010 | Garcia et al. |
| 7,823,221 | B2 | 11/2010 | Green |
| 7,942,856 | B2 | 5/2011 | Lentini |
| 7,959,671 | B2 | 6/2011 | Mangiardi et al. |
| 7,976,521 | B2 | 7/2011 | Hara et al. |
| 8,012,194 | B2 | 9/2011 | Edwin et al. |
| 8,066,657 | B2 | 11/2011 | Frazer |
| 8,206,436 | B2 | 6/2012 | Mangiardi et al. |
| 8,226,621 | B2 | 7/2012 | Timmons |
| 8,235,939 | B2 | 8/2012 | Johnson et al. |
| 8,262,719 | B2 | 9/2012 | Erickson et al. |
| 8,292,860 | B1 | 10/2012 | Persichetti et al. |
| 8,348,914 | B2 | 1/2013 | Zyburt et al. |
| 8,357,193 | B2 | 1/2013 | Phan et al. |
| 8,366,690 | B2 | 2/2013 | Locke et al. |
| 8,414,635 | B2 | 4/2013 | Hyodoh et al. |
| 8,425,539 | B2 | 4/2013 | Binmoeller et al. |
| 8,439,934 | B2 | 5/2013 | Satasiya et al. |
| 8,454,632 | B2 | 6/2013 | Binmoeller et al. |
| 8,518,099 | B2 | 8/2013 | Chanduszko et al. |
| 8,524,132 | B2 | 9/2013 | Von Oepen et al. |
| 8,535,366 | B2 | 9/2013 | Mangiardi et al. |
| 8,636,721 | B2 | 1/2014 | Alam et al. |
| 8,641,692 | B2 | 2/2014 | Tout et al. |
| 8,652,099 | B2 | 2/2014 | Fierens et al. |
| 8,677,874 | B2 | 3/2014 | Lilburn et al. |
| 8,696,611 | B2 | 4/2014 | Yaacov et al. |
| 8,715,334 | B2 | 5/2014 | Clerc et al. |
| 8,814,839 | B2 | 8/2014 | Christensen et al. |
| 8,834,558 | B2 | 9/2014 | Nissl |
| 8,906,081 | B2 | 12/2014 | Cully et al. |
| 8,926,683 | B2 | 1/2015 | Darla et al. |
| 8,961,448 | B2 | 2/2015 | Forsell |
| 8,992,492 | B2 | 3/2015 | Anderson et al. |
| 9,155,643 | B2 | 10/2015 | Clerc et al. |
| 9,192,496 | B2 | 11/2015 | Robinson |
| 9,259,336 | B2 | 2/2016 | Schaeffer et al. |

(56) References Cited

U.S. PATENT DOCUMENTS

| | | |
|---|---|---|
| 9,284,637 B2 | 3/2016 | Boyle et al. |
| 9,381,041 B2 | 7/2016 | Brown et al. |
| 10,285,834 B2 | 5/2019 | Cindrich et al. |
| 2001/0037141 A1 | 11/2001 | Yee et al. |
| 2002/0068037 A1 | 6/2002 | Platzet et al. |
| 2002/0099435 A1 | 7/2002 | Stinson |
| 2002/0138095 A1 | 9/2002 | Mazzocchi et al. |
| 2002/0151967 A1 | 10/2002 | Mikus et al. |
| 2002/0183827 A1 | 12/2002 | Derus et al. |
| 2002/0193749 A1 | 12/2002 | Olovson |
| 2003/0023268 A1 | 1/2003 | Lizardi |
| 2003/0028236 A1 | 2/2003 | Gillick |
| 2003/0050686 A1 | 3/2003 | Raeder-Devens et al. |
| 2003/0135265 A1 | 7/2003 | Stinson |
| 2003/0135268 A1 | 7/2003 | Desai |
| 2003/0144671 A1 | 7/2003 | Brooks et al. |
| 2003/0163101 A1 | 8/2003 | Say |
| 2003/0167060 A1 | 9/2003 | Buzzard et al. |
| 2004/0030381 A1 | 2/2004 | Shu |
| 2004/0098077 A1 | 5/2004 | Gianotti |
| 2004/0106977 A1* | 6/2004 | Sullivan ............ A61F 2/95 623/1.12 |
| 2004/0127973 A1 | 7/2004 | Mangiardi et al. |
| 2004/0181239 A1 | 9/2004 | Dorn et al. |
| 2004/0193243 A1 | 9/2004 | Mangiardi et al. |
| 2004/0267281 A1 | 12/2004 | Harari et al. |
| 2005/0004447 A1 | 1/2005 | Yamamoto |
| 2005/0027345 A1 | 2/2005 | Horan et al. |
| 2005/0038495 A1 | 2/2005 | Greenan |
| 2005/0090887 A1 | 4/2005 | Pryor |
| 2005/0125050 A1 | 6/2005 | Carter et al. |
| 2005/0149160 A1 | 7/2005 | McFerran |
| 2005/0182475 A1 | 8/2005 | Jen et al. |
| 2005/0278010 A1 | 12/2005 | Richardson |
| 2005/0283179 A1 | 12/2005 | Lentz |
| 2006/0020321 A1 | 1/2006 | Parker |
| 2006/0155368 A1 | 7/2006 | Shin |
| 2006/0184224 A1 | 8/2006 | Angel |
| 2006/0258972 A1 | 11/2006 | Mangiardi et al. |
| 2006/0259113 A1 | 11/2006 | Nissl |
| 2007/0005122 A1 | 1/2007 | Inoue |
| 2007/0043421 A1 | 2/2007 | Mangiardi et al. |
| 2007/0100421 A1 | 5/2007 | Griffin |
| 2007/0135904 A1 | 6/2007 | Eidenschink et al. |
| 2007/0156225 A1 | 7/2007 | George et al. |
| 2007/0179590 A1 | 8/2007 | Lu et al. |
| 2007/0208350 A1 | 9/2007 | Gunderson |
| 2007/0250150 A1 | 10/2007 | Pal et al. |
| 2007/0270932 A1 | 11/2007 | Headley et al. |
| 2008/0097572 A1 | 4/2008 | Sheldon et al. |
| 2008/0108948 A1 | 5/2008 | Beaver |
| 2008/0114443 A1 | 5/2008 | Mitchell et al. |
| 2008/0140178 A1 | 6/2008 | Rasmussen et al. |
| 2008/0177252 A1 | 7/2008 | Isik |
| 2008/0228256 A1 | 9/2008 | Erickson et al. |
| 2008/0288042 A1 | 11/2008 | Purdy et al. |
| 2009/0099636 A1 | 4/2009 | Chanduszko et al. |
| 2009/0099647 A1 | 4/2009 | Glimsdale et al. |
| 2009/0118740 A1 | 5/2009 | Mangiardi et al. |
| 2009/0143731 A1 | 6/2009 | Guzman |
| 2009/0157158 A1 | 6/2009 | Ondracek |
| 2009/0171427 A1 | 7/2009 | Melsheimer et al. |
| 2009/0171433 A1 | 7/2009 | Melsheimer |
| 2009/0187240 A1 | 7/2009 | Clerc |
| 2009/0192518 A1 | 7/2009 | Golden et al. |
| 2009/0292262 A1 | 11/2009 | Adams et al. |
| 2010/0023032 A1 | 1/2010 | Granja et al. |
| 2010/0023132 A1 | 1/2010 | Imran |
| 2010/0030256 A1 | 2/2010 | Dubrul et al. |
| 2010/0030321 A1 | 2/2010 | Mach |
| 2010/0049295 A1 | 2/2010 | Satasiya et al. |
| 2010/0057145 A1 | 3/2010 | Bhatnagar et al. |
| 2010/0057185 A1 | 3/2010 | Melsheimer et al. |
| 2010/0070016 A1 | 3/2010 | Dorn |
| 2010/0145431 A1 | 6/2010 | Wu et al. |
| 2010/0174227 A1 | 7/2010 | Ramella et al. |
| 2010/0198333 A1* | 8/2010 | Macatangay ............ A61F 2/88 623/1.15 |
| 2010/0252470 A1 | 10/2010 | Ryan et al. |
| 2010/0274229 A1 | 10/2010 | Duocastella Codina et al. |
| 2011/0004290 A1 | 1/2011 | Bales, Jr. et al. |
| 2011/0015616 A1 | 1/2011 | Straubinger et al. |
| 2011/0071623 A1 | 3/2011 | Finch et al. |
| 2011/0082464 A1 | 4/2011 | Douk et al. |
| 2011/0137396 A1 | 6/2011 | Dorn et al. |
| 2011/0137400 A1 | 6/2011 | Dorn et al. |
| 2011/0190710 A1 | 8/2011 | Miyoshi |
| 2011/0190862 A1 | 8/2011 | Mehran et al. |
| 2011/0208296 A1 | 8/2011 | Duffy et al. |
| 2011/0230863 A1 | 9/2011 | Lentini |
| 2011/0264191 A1 | 10/2011 | Rothstein |
| 2011/0288482 A1 | 11/2011 | Farrell et al. |
| 2011/0307070 A1 | 12/2011 | Clerc et al. |
| 2011/0313360 A1 | 12/2011 | Lin |
| 2011/0319980 A1 | 12/2011 | Ryan |
| 2012/0046729 A1 | 2/2012 | Von Oepen et al. |
| 2012/0095567 A1 | 4/2012 | Weisman et al. |
| 2012/0136426 A1 | 5/2012 | Phan et al. |
| 2012/0197203 A1 | 8/2012 | Nokes, Jr. et al. |
| 2012/0283679 A1 | 11/2012 | Berish et al. |
| 2012/0290066 A1 | 11/2012 | Nabulsi et al. |
| 2012/0296257 A1 | 11/2012 | Van Dan et al. |
| 2012/0303109 A1 | 11/2012 | Okuma |
| 2012/0303112 A1 | 11/2012 | Armstrong et al. |
| 2012/0310320 A1 | 12/2012 | Gill et al. |
| 2012/0330402 A1* | 12/2012 | Vad ............ A61F 2/88 623/1.13 |
| 2013/0018215 A1 | 1/2013 | Snider et al. |
| 2013/0060205 A1 | 3/2013 | Mansour et al. |
| 2013/0103163 A1 | 4/2013 | Krimsky et al. |
| 2013/0110221 A1 | 5/2013 | Campbell et al. |
| 2013/0116770 A1 | 5/2013 | Robinson |
| 2013/0116771 A1 | 5/2013 | Robinson |
| 2013/0116772 A1 | 5/2013 | Robinson et al. |
| 2013/0158673 A1 | 6/2013 | Toomey |
| 2013/0184833 A1 | 7/2013 | Ryan et al. |
| 2013/0197623 A1 | 8/2013 | McHugo |
| 2013/0226114 A1 | 8/2013 | Massi et al. |
| 2013/0231689 A1 | 9/2013 | Binmoeller et al. |
| 2013/0245585 A1 | 9/2013 | Letellier |
| 2013/0253546 A1 | 9/2013 | Sander et al. |
| 2013/0274870 A1 | 10/2013 | Lombardi et al. |
| 2013/0296814 A1 | 11/2013 | Antholz |
| 2013/0310833 A1 | 11/2013 | Brown et al. |
| 2014/0031735 A1 | 1/2014 | Zurovick |
| 2014/0074065 A1 | 3/2014 | Muni et al. |
| 2014/0074219 A1 | 3/2014 | Hingston et al. |
| 2014/0155744 A1 | 6/2014 | Pameijer |
| 2014/0162400 A1 | 6/2014 | Vail et al. |
| 2014/0171863 A1 | 6/2014 | Blacker |
| 2014/0194778 A1 | 7/2014 | Uziel et al. |
| 2014/0196792 A1 | 7/2014 | Torres-Leon |
| 2014/0236064 A1 | 8/2014 | Binmoeller et al. |
| 2014/0243992 A1 | 8/2014 | Walsh et al. |
| 2014/0249412 A1 | 9/2014 | Yamamoto |
| 2014/0277573 A1 | 9/2014 | Gill et al. |
| 2014/0288636 A1 | 9/2014 | Headley, Jr. et al. |
| 2014/0303709 A1 | 10/2014 | Dwork |
| 2014/0330305 A1 | 11/2014 | Rood et al. |
| 2014/0336744 A1* | 11/2014 | Tani ............ A61F 2/966 623/1.11 |
| 2014/0350694 A1 | 11/2014 | Behan |
| 2014/0364959 A1 | 12/2014 | Attar et al. |
| 2015/0066128 A1 | 3/2015 | Losordo et al. |
| 2015/0100133 A1 | 4/2015 | Xie et al. |
| 2015/0112377 A1 | 4/2015 | Arnone et al. |
| 2015/0173919 A1 | 6/2015 | Baldwin |
| 2015/0230955 A1 | 8/2015 | Farag Eells et al. |
| 2015/0297880 A1 | 10/2015 | Ogawa et al. |
| 2015/0313595 A1 | 11/2015 | Houshton et al. |
| 2015/0313599 A1 | 11/2015 | Johnson et al. |
| 2016/0032769 A1 | 2/2016 | Stutz et al. |
| 2016/0081823 A1 | 3/2016 | Majercak |
| 2016/0081832 A1 | 3/2016 | Hingston et al. |

(56) References Cited

U.S. PATENT DOCUMENTS

| | | |
|---|---|---|
| 2016/0242846 A1 | 8/2016 | Brown et al. |
| 2016/0256306 A1 | 9/2016 | Cindrich et al. |
| 2016/0310302 A1 | 10/2016 | Neglen et al. |
| 2017/0014133 A1 | 1/2017 | Han et al. |
| 2017/0035424 A1 | 2/2017 | Binmoeller et al. |
| 2017/0035426 A1 | 2/2017 | Phan et al. |
| 2017/0035427 A1 | 2/2017 | Sander et al. |
| 2017/0035428 A1 | 2/2017 | Binmoeller et al. |
| 2017/0112624 A1 | 4/2017 | Patel |
| 2017/0354404 A1 | 12/2017 | Chu |
| 2018/0185183 A1 | 7/2018 | Christakis et al. |
| 2018/0263797 A1 | 9/2018 | Eller et al. |
| 2018/0303594 A1 | 10/2018 | Eller et al. |
| 2019/0044174 A1 | 2/2019 | Zhu et al. |
| 2019/0099589 A1 | 4/2019 | Walsh et al. |
| 2020/0375768 A1 | 12/2020 | Eller et al. |
| 2022/0023026 A1 | 1/2022 | Eller et al. |
| 2022/0125608 A1 | 4/2022 | Ethridge et al. |
| 2022/0211527 A1 | 7/2022 | Mower et al. |
| 2023/0381000 A1 | 11/2023 | Eller et al. |
| 2023/0381003 A1 | 11/2023 | Elwood et al. |

FOREIGN PATENT DOCUMENTS

| | | |
|---|---|---|
| DE | 4323866 | 1/1994 |
| DE | 102005051469 | 4/2007 |
| EP | 0364420 | 4/1990 |
| EP | 0408245 | 1/1991 |
| EP | 0872220 | 10/1998 |
| EP | 1637092 | 3/2006 |
| EP | 2522316 | 11/2012 |
| GB | 2243786 | 9/1989 |
| JP | H10305050 A | 11/1998 |
| JP | 2002525168 A | 8/2002 |
| JP | 2016032769 A | 3/2016 |
| WO | 1993022986 | 11/1993 |
| WO | 199631174 | 10/1996 |
| WO | 200018330 | 4/2000 |
| WO | 2000078246 | 12/2000 |
| WO | 2002056798 | 7/2002 |
| WO | 2002087470 | 11/2002 |
| WO | 2003090644 | 11/2003 |
| WO | 2004030571 | 4/2004 |
| WO | 2005070095 | 8/2005 |
| WO | 2008042266 | 4/2008 |
| WO | 2010130297 | 11/2010 |
| WO | 2011067280 A1 | 6/2011 |
| WO | 2012062603 | 10/2012 |
| WO | 2013045262 | 4/2013 |
| WO | 2013052528 | 4/2013 |
| WO | 2013066883 | 10/2013 |
| WO | 2015184154 | 12/2015 |
| WO | 2016141295 A1 | 9/2016 |
| WO | 2019099080 | 5/2019 |
| WO | 2020146261 | 7/2020 |

OTHER PUBLICATIONS

Office Action dated May 21, 2021 for U.S. Appl. No. 15/921,220.
Notice of Allowance dated Jan. 5, 2023 for U.S. Appl. No. 15/921,220.
Office Action dated Nov. 25, 2022 for U.S. Appl. No. 16/994,260.
European Search Report dated Dec. 15, 2020 for EP18768455.0.
Office Action dated Dec. 22, 2020 for U.S. Appl. No. 15/921,220.
European Examination Report dated Feb. 2, 2023 for EP18768455.0.
Notice of Allowance dated Mar. 15, 2023 for U.S. Appl. No. 16/994,260.
European Search Report dated Apr. 9, 2018 for EP15860892.7.
European Search Report dated Nov. 9, 2020 for EP18767753.9.
International Publication and Search Report dated Aug. 4, 2005 for WO2005070095.
International Search Report and Written Opinion dated Feb. 14, 2022 for PCT/US2021/056495.
Office Action dated Dec. 2, 2019 for U.S. Appl. No. 15/718,419.
International Search Report and Written Opinion dated Sep. 12, 2016 for PCT/US2016/040174.
International Search Report and Written Opinion dated Nov. 9, 2021 for PCT/US2021/042833.
Office Action dated Nov. 9, 2021 for U.S. Appl. No. 15/921,221.
Notice of Allowance dated Jul. 22, 2020 for U.S. Appl. No. 15/718,419.
Office Action dated Apr. 15, 2022 for U.S. Appl. No. 15/921,220.
Office Action dated Apr. 23, 2020 for U.S. Appl. No. 15/596,823.
Office Action dated Jun. 23, 2020 for U.S. Appl. No. 15/696,440.
Office Action dated Oct. 16, 2019 for U.S. Appl. No. 15/596,823.
European Search Report dated Mar. 19, 2021 for EP18768455.0.
International Search Report and Written Opinion dated Aug. 2, 2018 for PCT/US2018/028107.
International Search Report and Written Opinion dated Sep. 28, 2005 for PCT/US2005/000515.
International Search Report and Written Opinion dated Oct. 29, 2009 for PCT/US2009/052691.
International Search Report and Written Opinion dated Nov. 23, 2006 for PCT/US2006/018811.
Notice of Allowance dated Jan. 14, 2015 for U.S. Appl. No. 11/432,964.
Notice of Allowance dated Feb. 25, 2019 for U.S. Appl. No. 15/061,107.
Notice of Allowance dated Mar. 6, 2013 for U.S. Appl. No. 12/535,980.
Notice of Allowance dated Jun. 11, 2013 for U.S. Appl. No. 10/585,430.
Notice of Allowance dated Jun. 22, 2016 for U.S. Appl. No. 13/664,267.
Notice of Allowance dated Aug. 12, 2015 for U.S. Appl. No. 13/664,200.
Notice of Allowance dated Sep. 6, 2018 for U.S. Appl. No. 29/597,873.
Notice of Allowance dated Sep. 11, 2019 for U.S. Appl. No. 15/263,741.
Notice of Allowance dated Sep. 23, 2016 for U.S. Appl. No. 13/664,234.
Notice of Allowance dated Oct. 21, 2014 for U.S. Appl. No. 13/313,929.
Office Action dated Jan. 3, 2014 for U.S. Appl. No. 11/432,964.
Office Action dated Jan. 22, 2013 for U.S. Appl. No. 10/585,430.
Office Action dated Jan. 31, 2012 for U.S. Appl. No. 10/585,430.
Office Action dated Feb. 5, 2020 for U.S. Appl. No. 15/921,172.
Office Action dated Mar. 6, 2020 for U.S. Appl. No. 15/955,895.
Office Action dated Mar. 16, 2015 for U.S. Appl. No. 13/664,234.
Office Action dated Mar. 22, 2016 for U.S. Appl. No. 13/664,234.
Office Action dated Mar. 24, 2015 for U.S. Appl. No. 13/664,267.
Office Action dated Apr. 6, 2016 for U.S. Appl. No. 13/664,137.
Office Action dated Apr. 7, 2020 for U.S. Appl. No. 15/955,895.
Office Action dated Apr. 25, 2018 for U.S. Appl. No. 15/061,107.
Office Action dated May 5, 2014 for U.S. Appl. No. 13/313,929.
Office Action dated May 25, 2012 for U.S. Appl. No. 12/535,980.
Office Action dated May 30, 2019 for U.S. Appl. No. 15/263,741.
Office Action dated Jun. 7, 2011 for U.S. Appl. No. 10/585,430.
Office Action dated Jul. 9, 2009 for U.S. Appl. No. 11/432,964.
Office Action dated Jul. 25, 2013 for U.S. Appl. No. 11/432,964.
Office Action dated Aug. 13, 2012 for U.S. Appl. No. 10/585,430.
Office Action dated Sep. 19, 2018 for U.S. Appl. No. 15/061,107.
Office Action dated Oct. 7, 2015 for U.S. Appl. No. 13/664,234.
Office Action dated Oct. 16, 2017 for U.S. Appl. No. 15/061,107.
European Examination Report dated Feb. 18, 2015 for EP09791142.4.
European Search Report dated Apr. 24, 2020 for EP17857414.1.
European Search Reported Sep. 24, 2018 for EP16759580.
International Preliminary Report dated May 15, 2014 for PCT/US2012/062603.
International Publication and Search Report Jun. 14, 2012 for WO2012078794.
International Publication and Search Report dated Feb. 25, 2012 for WO2010021836.

(56) References Cited

OTHER PUBLICATIONS

International Search Report and Written Opinion dated Jan. 9, 2018 for PCT/US2017/054000.
International Search Report and Written Opinion dated Mar. 16, 2012 for PCT/US2011/063799.
International Search Report and Written Opinion dated Mar. 29, 2013 for PCT/US2012/062603.
International Search Report and Written Opinion dated Jun. 22, 2016 for PCT/US2016/020900.
International Search Report and Written Opinion dated Jun. 29, 2018 for PCT/US2018/022340.
International Search Report and Written Opinion dated Jun. 29, 2018 for PCT/US2018/022344.
Office Action dated Nov. 9, 2010 for U.S. Appl. No. 10/585,430.
Office Action dated Nov. 14, 2012 for U.S. Appl. No. 12/535,980.
Office Action dated Nov. 14, 2018 for U.S. Appl. No. 15/263,741.
Office Action dated Nov. 19, 2015 for U.S. Appl. No. 13/664,137.
Office Action dated Nov. 30, 2016 for U.S. Appl. No. 13/664,137.
Office Action dated Dec. 7, 2009 for U.S. Appl. No. 11/432,964.
Office Action dated Dec. 8, 2009 for U.S. Appl. No. 10/585,430.
Cheon, et al., Clinical Feasibility of a New Through-The-Scope Fully Covered Esophageal Self-Expandable Metallic Stent: An in Vivo Animal Study, Digestive Endoscopy, vol. 26 No. 1 ,2014 , 32-36.
Kawakami, et al., Endoscopic Ultrasound-Guided Transluminal Drainage for Peripancreatic Fluid Collections: Where are we now?, Gut and Liver, vol. 8 No. 4 ,2014 , 341-355.
Sen, et al., Laplace's Equation for Convective Scalar Transport in Potential Flow, Proc. R. Soc. Lond. A 456, pp. 3041-3045 ,2000.
Sizarov, et al., Novel materials and Devices in the Transcatheter Creation of vascular Anastomosis—The Future Comes Slowly (Part 2), Archives of Cardiovascular Diseases, vol. 109 No. 4 ,2016 , 286-295.
Weilert, et al., Specially Designed Stents for Translumenal Drainage, Gastrointestinal Intervention, vol. 4 No. 1 ,2015,40-45.
Office Action dated Sep. 10, 2024 for U.S. Appl. No. 18/301,717.
European Search Report dated Nov. 5, 2024 for EP24175441.5.
Office Action dated Nov. 7, 2024 for U.S. Appl. No. 17/655,846.

\* cited by examiner

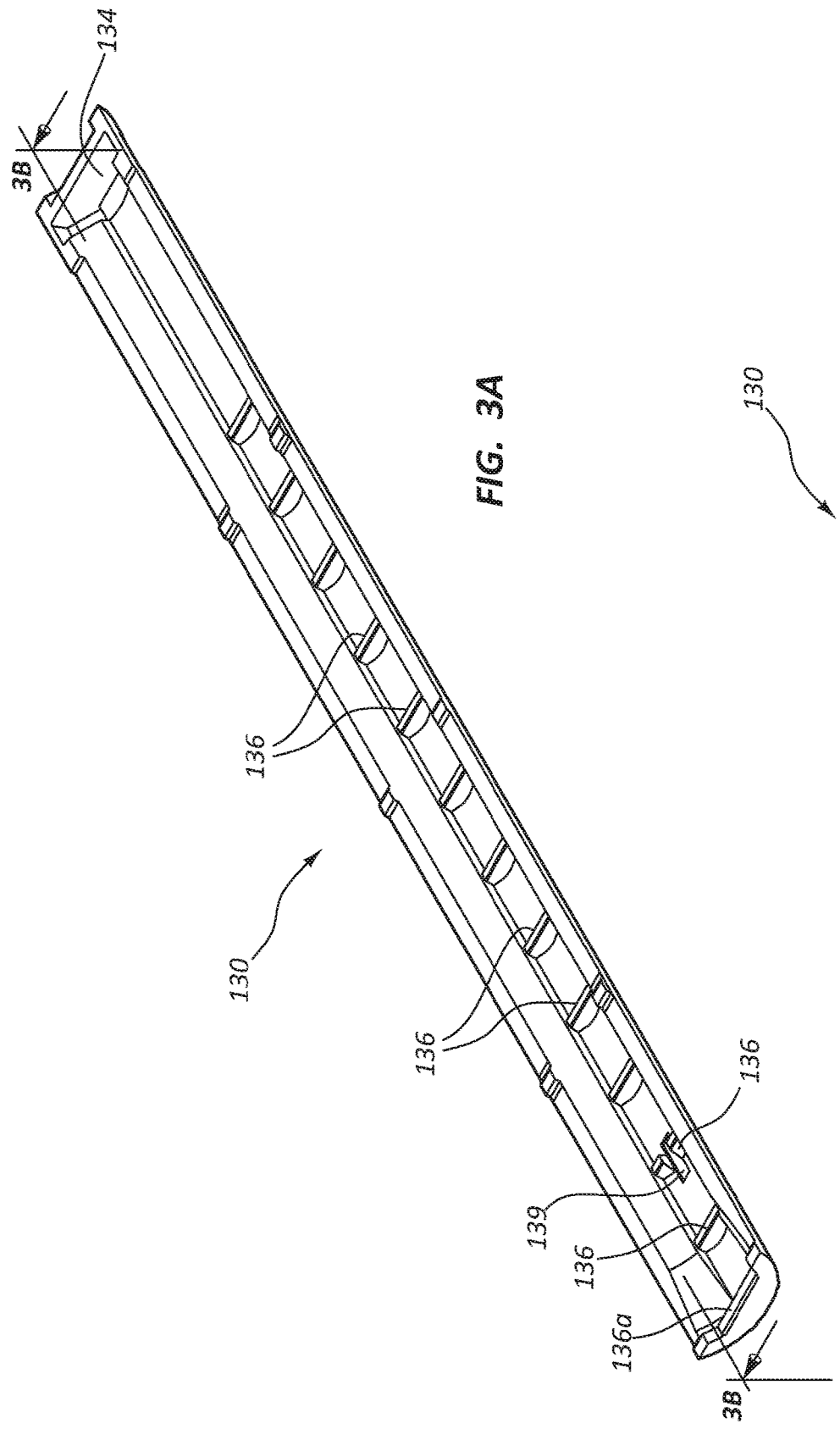
FIG. 3A
FIG. 3B

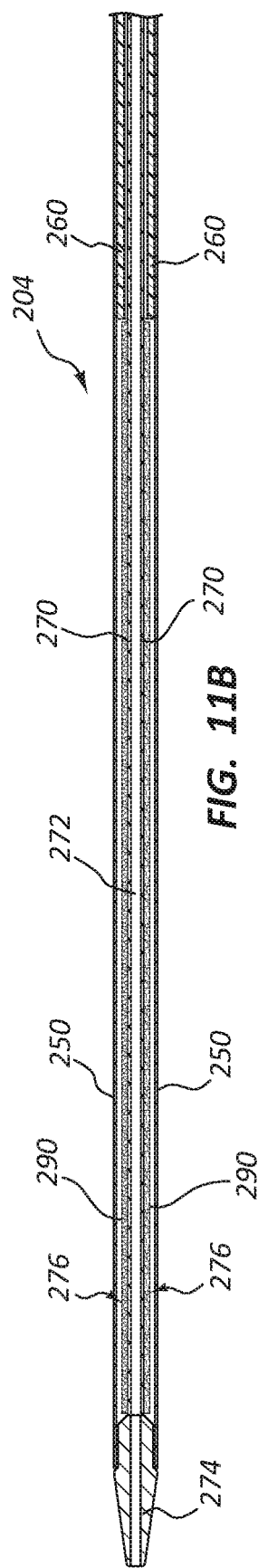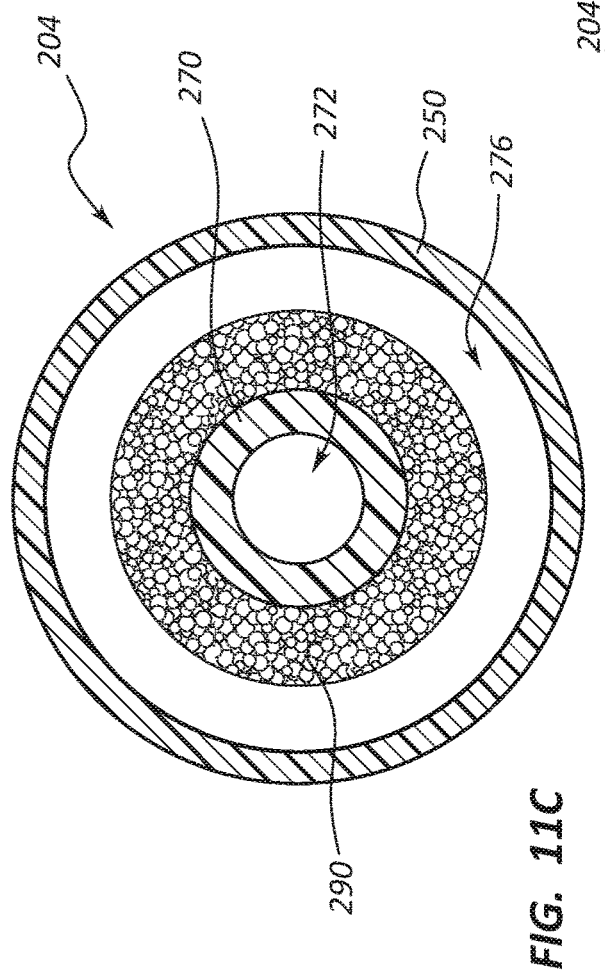
FIG. 11B
FIG. 11C
FIG. 11D

PLIANT MEMBERS FOR RECEIVING AND AIDING IN THE DEPLOYMENT OF VASCULAR PROSTHESES

RELATED APPLICATIONS

This application is a continuation of U.S. patent application Ser. No. 15/718,419, filed on Sep. 28, 2017 and titled, "Pliant Members for Receiving and Aiding in the Deployment of Vascular Prostheses," which claims priority to U.S. Provisional Application No. 62/401,628 filed on Sep. 29, 2016 and titled, "Pliant Members for Receiving and Aiding in the Deployment of Vascular Prostheses," both of which are hereby incorporated by reference in their entireties.

TECHNICAL FIELD

The present disclosure relates generally to medical devices. More specifically, the present disclosure relates to vascular prosthesis deployment devices, including deployment devices for self-expanding vascular prostheses such as stents and stent-grafts.

BRIEF DESCRIPTION OF THE DRAWINGS

The embodiments disclosed herein will become more fully apparent from the following description and appended claims, taken in conjunction with the accompanying drawings. The drawings depict only typical embodiments, which embodiments will be described with additional specificity and detail in connection with the drawings in which:

FIG. 3A is a perspective view of a ratchet slide component of the deployment device of FIGS. 1 and 2.

FIG. 3B is a cross-sectional view of the ratchet slide of FIG. 3A.

FIG. 11B is a cross-sectional view of a portion of a delivery catheter assembly of the deployment device of FIG. 11A along plane 11B-11B.

FIG. 11C is a cross-sectional view of a portion of the delivery catheter assembly of the deployment device of FIG. 11A along plane 11C-11C.

FIG. 11D is a side view of another portion of the delivery catheter assembly of the deployment device of FIG. 11A.

DETAILED DESCRIPTION

Figure 1:
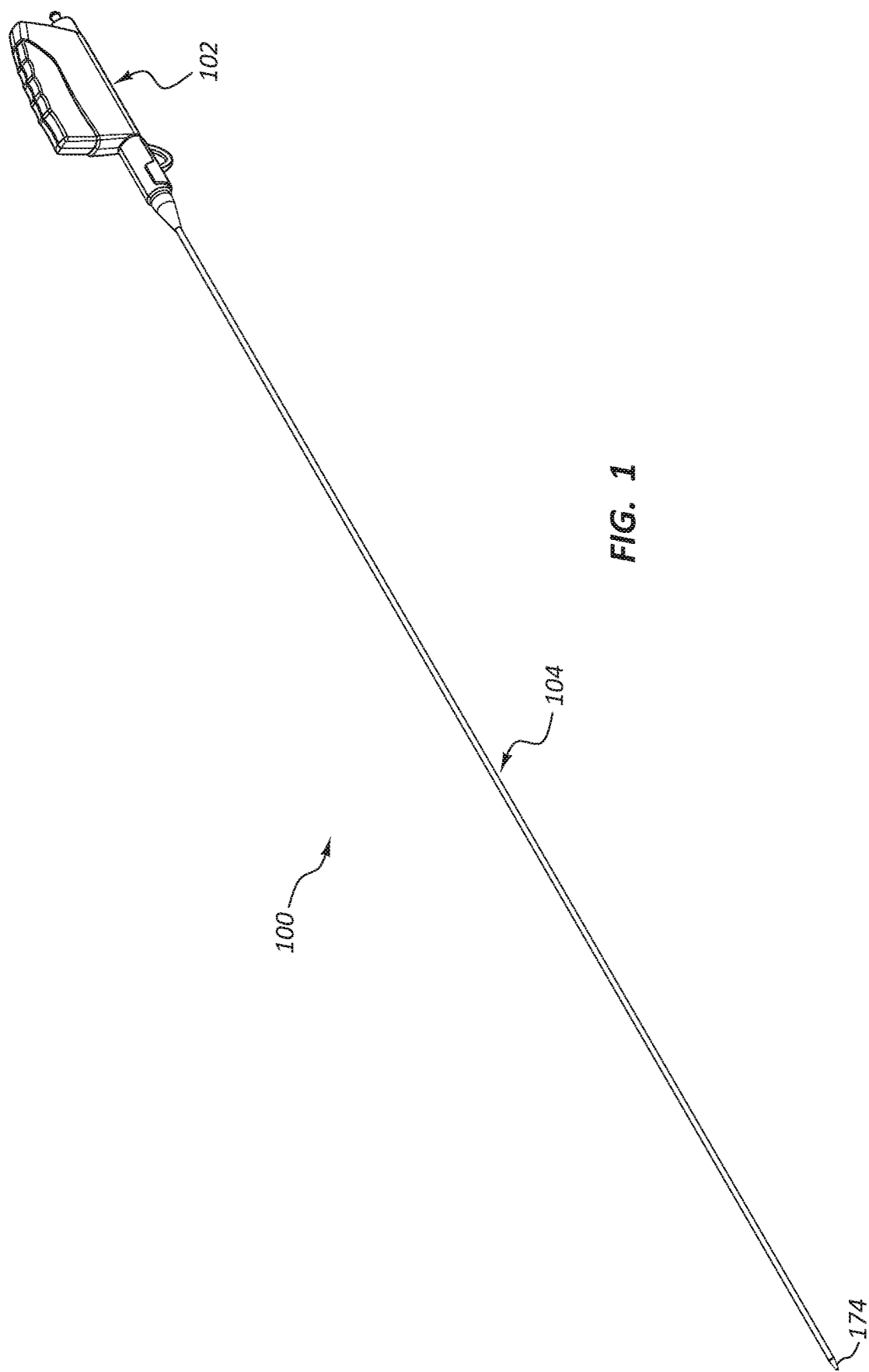
FIG. 1 is a perspective view of a deployment device.

Deployment devices may be configured to deliver a medical appliance to a location within a patient's body and deploy the medical appliance within the patient's body. Though specific examples recited herein may refer to deployment of devices within the vasculature, analogous concepts and devices may be used in various other locations within the body, including for placement and deployment of medical appliances in the gastrointestinal tract (including, for example, within the esophagus, intestines, stomach, small bowel, colon, and biliary duct); the respiratory system (including, for example, within the trachea, bronchial tubes, lungs, nasal passages, and sinuses); or any other location within the body, both within bodily lumens (for example, the ureter, the urethra, and/or any of the lumens discussed above) and within other bodily structures.

Furthermore, though specific examples herein may refer to deployment of vascular prostheses such as stents, deployment of a wide variety of medical appliances are within the scope of this disclosure, including stents, stent-grafts, shunts, grafts, and so forth. Additionally, the deployment device disclosed herein may be configured to deliver and deploy self-expanding medical appliances, including stents configured to expand within a bodily lumen upon deployment.

As used herein, delivery of a medical appliance generally refers to placement of a medical appliance in the body, including displacement of the appliance along a bodily lumen to a treatment site. For example, delivery includes displacement of a crimped stent along a vascular lumen from an insertion site to a treatment location. Deployment of a medical appliance refers to placement of the medical appliance within the body such that the medical appliance interacts with the body at the point of treatment. For example, deployment includes releasing a crimped or otherwise constrained self-expanding stent from a deployment device such that the stent expands and contacts a lumen of the vasculature.

Deployment devices within the scope of this disclosure may be configured to incrementally deploy a medical appliance. Incremental deployment may facilitate desired placement of the medical appliance due to the degree of control afforded a practitioner during deployment. A practitioner may, for example, desire to deploy a portion of a stent, make adjustments to placement within the vasculature or confirm the location of the stent, prior to deploying the remaining portion of the stent. Such processes may be iterative, with a practitioner deploying a portion of a stent, confirming placement, deploying an additional portion, again confirming placement, and so forth until the stent is fully deployed.

Deployment devices within the scope of this disclosure may be configured to provide visual, audible, tactile, or other feedback relating to the degree to which a medical appliance has been deployed. Multiple types of feedback may enhance a practitioner's level of control over the procedure due to the multiple indications regarding location or degree of deployment of the medical appliance.

Moreover, deployment devices within the scope of this disclosure may provide a degree of mechanical advantage during deployment, for example, through the use of levers to decrease the force used to deploy a device. Mechanical advantage may thus increase a user's comfort and level of control during use. Still further, deployment devices within the scope of this disclosure may be ergonomically designed, presenting an actuation input disposed such that a practitioner can directly engage and utilize the device, without repositioning his or her hand or body. Deployment devices within the scope of this disclosure may also be configured for one-handed actuation and may be configured for ambidextrous use.

It will be readily understood that the components of the embodiments as generally described and illustrated in the figures herein could be arranged and designed in a wide variety of configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

The phrases "connected to" and "coupled to" refer to any form of interaction between two or more entities, including mechanical, electrical, magnetic, electromagnetic, fluidic, and thermal interaction. Two components may be coupled to each other even though they are not in direct contact with each other. For example, two components may be coupled to each other through an intermediate component.

The directional terms "proximal" and "distal" are used herein to refer to opposite locations on a medical device. The proximal end of the device is defined as the end of the device closest to the practitioner when the device is in use by the practitioner. The distal end is the end opposite the proximal end, along the longitudinal direction of the device, or the end furthest from the practitioner.

Again, though the embodiments specifically described below may reference a stent deployment device specifically, the concepts, devices, and assemblies discussed below may be analogously applied to deployment of a wide variety of medical appliances in a wide variety of locations within the body.

FIG. 1 is a perspective view of a deployment device 100. The deployment device 100 comprises a handle assembly 102 adjacent the proximal end of the deployment device 100. An elongate delivery catheter assembly 104 extends distally from the handle assembly 102 to a distal tip or delivery tip 174. The handle assembly 102 may provide a proximal user input, with one or more components configured to allow a practitioner to deploy or otherwise manipulate a stent disposed within the delivery catheter assembly 104.

In use, the handle assembly 102 may be disposed outside of a patient's body, while the delivery catheter assembly 104 is advanced to a treatment location within the patient's body. For example, the delivery catheter assembly 104 may be advanced from an insertion site (such as, for example, a femoral or jugular insertion site) to a treatment location within the vasculature. As further detailed below, the delivery catheter assembly 104 may be configured to be advanced through bends, turns, or other structures within the anatomy of the vasculature. Again, as detailed below, a stent may be disposed within a portion of the delivery catheter assembly 104 such that a practitioner may deploy the stent from a distal end of the delivery catheter assembly 104 through manipulation of one or more components of the handle assembly 102.

Figure 2:
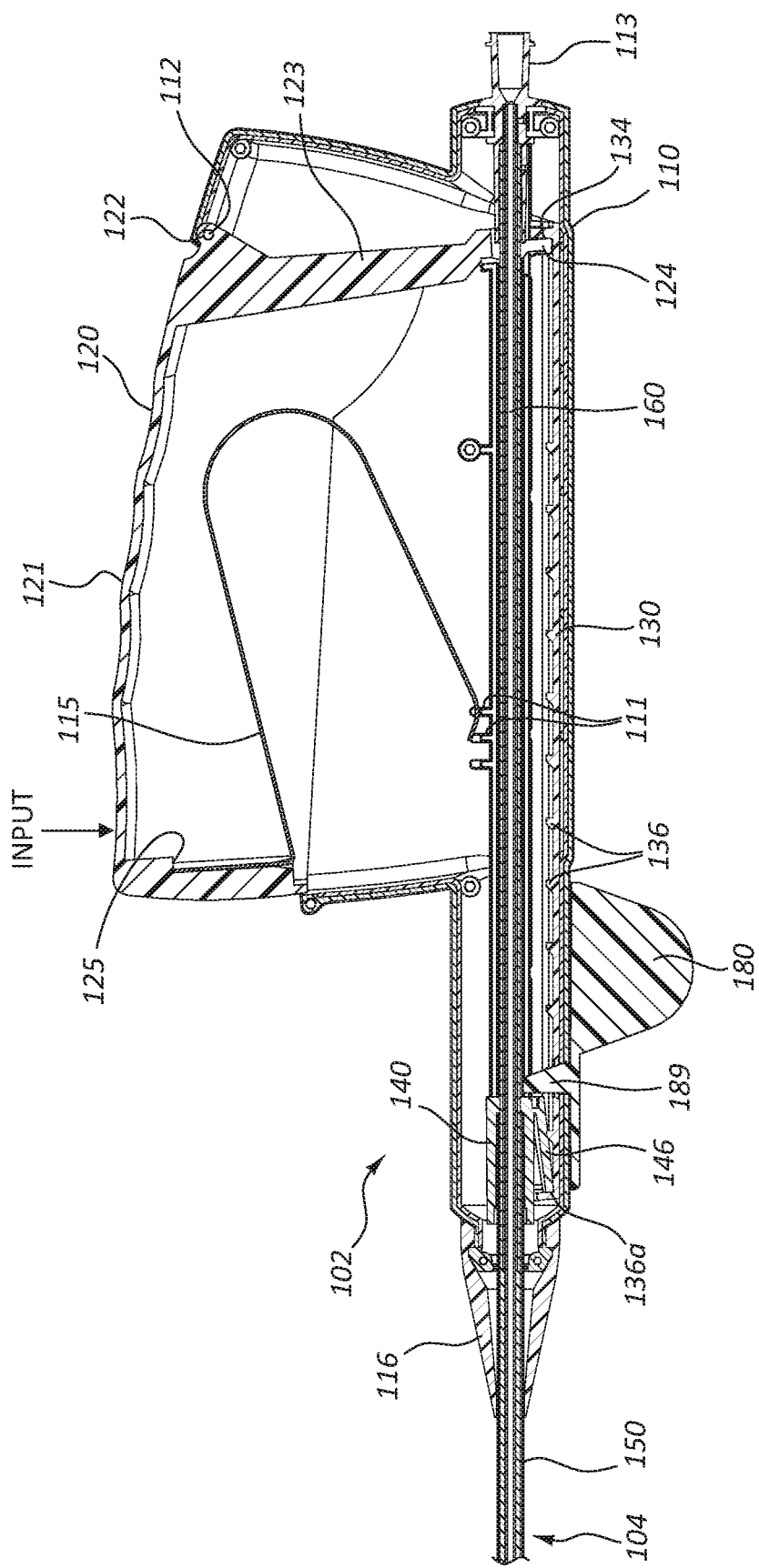
FIG. 2 is a cross-sectional view of a portion of the deployment device of FIG. 1.

FIG. 2 is a cross-sectional view of a portion of the deployment device 100 of FIG. 1. Specifically, FIG. 2 is a side view of a portion of the deployment device 100 of FIG. 1, taken through a cross-sectional plane extending vertically and intersecting a longitudinal axis of the deployment device 100, when the deployment device 100 is positioned as shown in FIG. 1. The longitudinal axis of the deployment device 100 extends along the center of the delivery catheter assembly 104, including along the center of components of the delivery catheter assembly 104 which overlap with the handle assembly 102, such as the intermediate sheath 160, as shown in FIG. 2.

As the handle assembly 102 is configured to be grasped or otherwise manipulated by a user and the delivery catheter assembly 104 is configured to extend to a treatment location within a patient's body, along the longitudinal axis, the delivery catheter assembly 104 extends in a distal direction away from the handle assembly 102. The proximal direction is opposite, correlating to a direction defined along the longitudinal axis, extending from the distal tip 174 toward the handle assembly 102.

FIG. 2 depicts various internal components of the handle assembly 102, exposed by the cross-sectional view. A portion of the delivery catheter assembly 104 is also shown extending from the handle assembly 102. The handle assembly 102 comprises a housing 110. The housing 110 surrounds certain components of the handle assembly 102, as shown, providing a grip surface for a practitioner.

The housing 110 is operably coupled to an actuator 120. Manipulation of the actuator 120 with respect to the housing 110 may be configured to deploy the stent, as further detailed below. In the depicted embodiment, the actuator 120 is rotatably coupled to the housing 110 by a pin 112. The pin 112 extends from the housing 110 and may be integrally formed with one or more other portions of the housing 110. As shown, the pin 112 extends through a pin aperture 122 in the actuator 120.

Other arrangements for operably coupling the actuator 120 and the housing 110 are within the scope of this disclosure. For example, the pin 112 may be integral with a portion of the actuator 120 and may be received in an opening, sleeve, or aperture formed in the housing 110. Other types of designs of rotatable couplings, including a separate coupling component such as a hinge are within the scope of this disclosure. Still further, a compliant mechanism, such as a deformable flange, may be utilized to rotatably couple the actuator 120 and the housing 110, including compliant couplings integrally formed with the actuator 120, the housing 110, or both. Moreover, it is within the scope of this disclosure to slidably couple an actuator (such as actuator 120) to a housing (such as housing 110). Configurations wherein the actuator 120 is manipulated through rotation, translation, or other displacement relative to the housing 110 are all within the scope of this disclosure.

The actuator 120 comprises an input portion 121 extending from the aperture 122. In the depicted embodiment, the input portion 121 comprises a surface, at least partially exposed with respect to the housing 110. In operation, a user may manipulate the actuator 120 by exerting a force on the input portion 121, illustrated by the arrow labeled "input" in FIG. 2, displacing the input portion 121 generally toward the longitudinal axis of the deployment device (100 of FIG. 1) and causing the actuator 120 to rotate about the pin 112 with respect to the housing 110. Displacement of the actuator 120 due to a force such as illustrated by the arrow labeled "input" corresponds to "depression" of the actuator 120 or "depression of the actuator 120 with respect to the housing 110."

The actuator 120 may further comprise a transfer arm 123 extending from the pin aperture 122. The transfer arm 123 may be rigidly coupled to the input portion 121, including embodiments wherein both the transfer arm 123 and the input portion 121 are integrally formed with the rest of the actuator 120. The transfer arm 123 extends to a ratchet slide engaging portion 124. Depression of the input portion 121, in the direction shown by the arrow labeled "input" displaces the transfer arm 123 as the actuator 120 is rotated about the pin 112.

Depression of the input portion 121 thus causes displacement of the ratchet slide engaging portion 124 with respect to the housing 110. This displacement of the ratchet slide engaging portion 124 can be understood as rotation about the pin 112 having a proximal translation component and a vertical translation component, as rotation of the input portion 121 in the direction indicated by the arrow labeled "input" will displace (with respect to the housing 110) the ratchet slide engaging portion 124 both proximally and vertically.

A spring 115 may be disposed between the actuator 120 and the housing 110. The spring 115 may be configured to resist displacement of the actuator 120 in the direction indicated by the arrow labeled "input" and may be configured to return the actuator to the relative position shown in FIG. 2 after it has been depressed by a user. When the handle assembly 102 is unconstrained, the spring 115 may thus maintain (or return to) the relative position of the actuator 120 with respect to the housing 110 as shown in FIG. 2.

In the illustrated embodiment, the spring 115 engages with a spring ledge 125 of the actuator 120 and spring protrusions 111 of the housing 110. The spring protrusions 111 may provide a bearing surface for the spring 115 offset from movable internal components of the handle assembly 102 (such as a carrier 140 further detailed below). Though three spring protrusions 111 are shown in the depicted embodiment, more or fewer protrusions, or use of other features such as ridges, ledges, shoulders, and so forth are within the scope of this disclosure.

The depicted embodiment comprises a leaf spring 115. Other biasing elements, such as coil springs, piston assemblies, compliant mechanisms, and so forth are likewise within the scope of this disclosure. In some instances, a compliant portion of one or both of the housing 110 and actuator 120 may provide a biasing force analogous to that provided by the spring 115. Leaf springs, such as spring 115, may be configured to provide a relatively constant biasing force notwithstanding compression of the spring 115 as the actuator 120 is rotated or depressed with respect to the housing 110.

As the actuator 120 is depressed with respect to the housing 110, the spring 115 compresses and the ratchet slide engaging portion 124 is displaced as described above. Again, the displacement of the ratchet slide engaging portion 124 with respect to the housing 110 can be understood as having a proximal component and a vertical component.

The ratchet slide engaging portion 124 may be operably coupled to a ratchet slide 130 such that displacement of the ratchet slide engaging portion 124 likewise displaces the ratchet slide 130. The ratchet slide 130 may be constrained such that the ratchet slide 130 is configured only for proximal or distal displacement with respect to the housing 110. Thus, operable coupling of the ratchet slide engaging portion 124 to the ratchet slide 130 may allow for sliding interaction between the ratchet slide engaging portion 124 and the ratchet slide 130 such that only the proximal or distal component of the displacement of the ratchet slide engaging portion 124 is transferred to the ratchet slide 130. Stated another way, the ratchet slide 130 may be displaced in a direction parallel to the longitudinal axis of the deployment device 100 while the input displacement may be at an angle to the longitudinal axis of the deployment device 100. It is noted that, in the configuration shown in FIG. 2, a safety member 180 may prevent proximal displacement of the ratchet slide 130. The safety member 180, including removal thereof, is discussed in more detail below. Discussion herein relating to displacement of the ratchet slide 130 and related components may thus be understood as disclosure relevant to a configuration of the handle assembly 102 in which the safety member 180 has been removed.

As the actuator 120 is depressed with respect to the housing 110, the ratchet slide 130 may thus be proximally displaced with respect to the housing 110. One or both of the ratchet slide 130 and actuator 120 may also interact with the housing 110 such that there is a positive stop to arrest the depression of the actuator 120 and/or proximal displacement of the ratchet slide 130. This positive stop may be an engaging ledge, shoulder, lug, detent, or other feature coupled to the housing 110, including features integrally formed on the housing 110.

A full stroke of the actuator 120 may thus correspond to displacement from the unconstrained position shown in FIG. 2, to the positive stop caused by interaction with the housing 110 when the actuator 120 is depressed. Release of the actuator 120 following a full or a partial stroke may then result in a return of the actuator 120 to the unconstrained state, due to the biasing force provided by the spring 115. The unconstrained state shown in FIG. 2 refers to lack of constraint due to user input. In this state, the spring 115 may be partially compressed, and interaction between the actuator 120 and the housing 110 may prevent rotation of the actuator 120 about the pin 112 in the opposite direction to depression of the actuator 120, or the return direction. In other words, interaction between the actuator 120 and the housing 110 (or features of the housing 110) may create a positive stop to the return motion of the actuator 120 as well.

Referring to both FIGS. 1 and 2, the actuator 120 and the housing 110 may be coupled such that pinching of external materials (such as a practitioner's hand or a surgical drape) is minimized when the actuator 120 is depressed or returned. For instance, the actuator 120 may comprise a shell configured to mate with, and slide into, the housing 110. Though the components may slide and rotate with respect to each other, the interface of the components may be sufficiently close and/or smooth to minimize pinching or other engagement of external materials. This close and/or smooth interface may refer to interaction at the edges of the actuator 120 as it is displaced into the housing 110 and/or to interaction at the portion of the actuator 120 near the pin 112, as the actuator 120 returns to the unconstrained position.

As also shown in FIGS. 1 and 2, the input portion 121 of the actuator 120 may also comprise ridges or other features to facilitate handling or gripping of the actuator 120 during use.

Referring again to FIG. 2, the ratchet slide 130 may thus be proximally displaced during depression of the actuator 120. Again, such displacement may correspond to a configuration in which the safety member 180 shown in FIG. 2 has been removed. Proximal displacement of the ratchet slide 130 may also proximally displace the carrier 140 due to interaction between one or more carrier engaging ratchet lugs 136 on the ratchet slide 130 and a ratchet slide engaging arm 146 coupled to the carrier 140.

FIG. 3A is a perspective view of the ratchet slide 130 of the deployment device 100 of FIGS. 1 and 2. FIG. 3B is a cross-sectional view of the ratchet slide 130 of FIG. 3A, taken through a vertical plane disposed along a longitudinal centerline of the ratchet slide 130. When the ratchet slide 130 is disposed within the handle assembly 102 of FIG. 2, this cross-sectional plane would intersect the longitudinal axis of the deployment device 100.

As shown in FIGS. 2, 3A, and 3B, the ratchet slide 130 may comprise a plurality of carrier engaging ratchet lugs 136. The carrier engaging ratchet lugs 136 may be spaced at even intervals along the longitudinal direction of the ratchet slide 130. In the figures, exemplary carrier engaging ratchet lugs are denoted with reference numeral 136, while the distal most carrier engaging ratchet lug, disposed at the distal end of the ratchet slide 130 is denoted with reference numeral 136a.

The ratchet slide 130 further comprises a ratchet slide safety opening 139 and an actuator engaging opening 134. These features are discussed in more detail below.

As noted above, interaction between the ratchet slide engaging portion 124 of the actuator 120 and the ratchet slide 130 may proximally displace the ratchet slide 130 with respect to the housing 110. Engagement between the carrier 140 and one of the carrier engaging ratchet lugs 136 may also proximally displace the carrier 140 as the ratchet slide 130 is proximally displaced with respect to the housing 110. In the configuration of FIG. 2, the ratchet slide engaging arm 146 of the carrier 140 is engaged with the distal most carrier engaging ratchet lug 136a.

Figure 4:
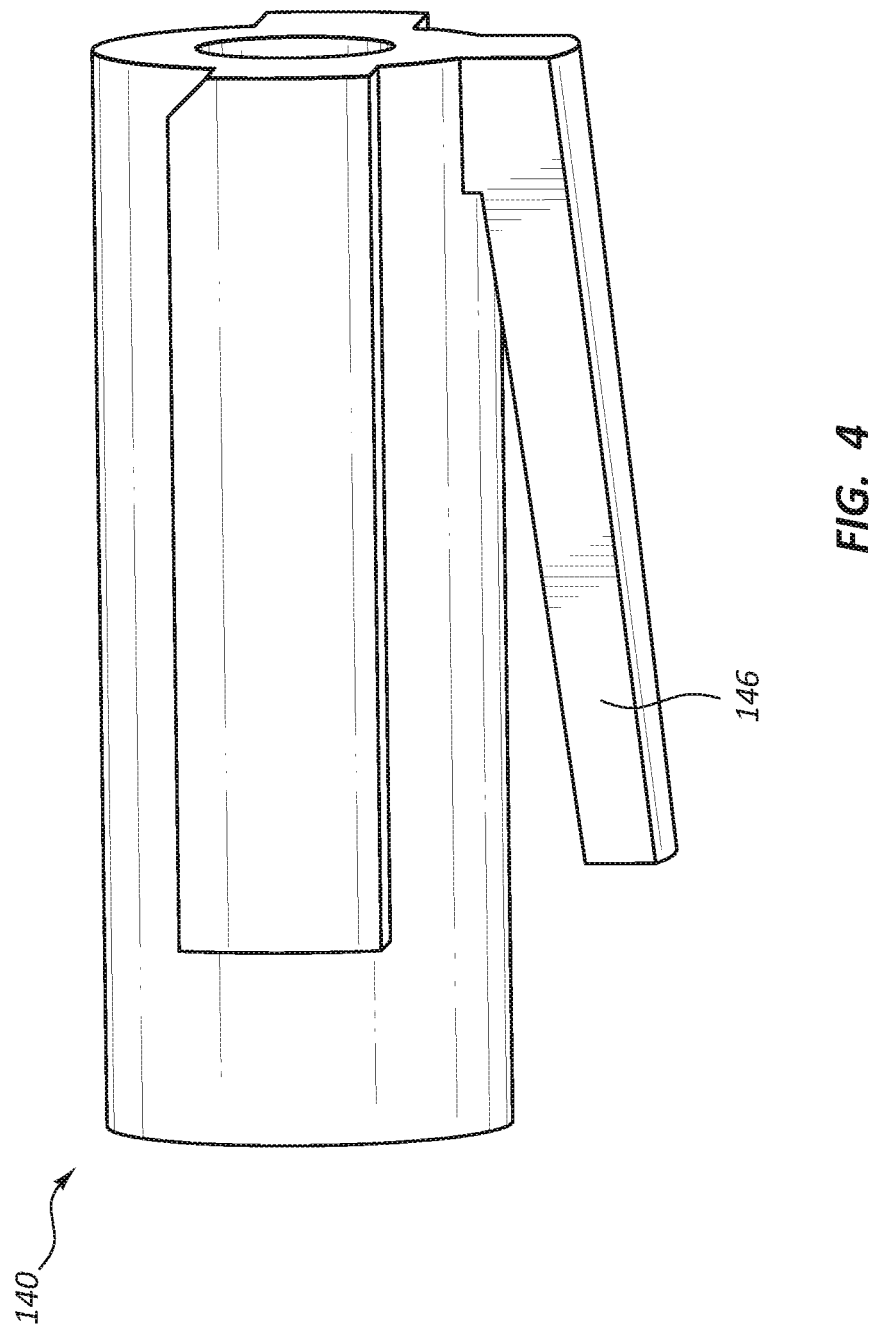
FIG. 4 is a side view of a carrier component of the deployment device of FIGS. 1 and 2.

FIG. 4 is a side view of the carrier 140 of the deployment device 100 of FIGS. 1 and 2. As shown in FIG. 4, the ratchet slide engaging arm 146 extends radially away from a longitudinal axis of the carrier 140. When the carrier 140 is disposed within the handle assembly 102 of FIG. 2, the longitudinal axis of the carrier 140 is disposed along the longitudinal axis of the deployment device 100.

Figure 5:
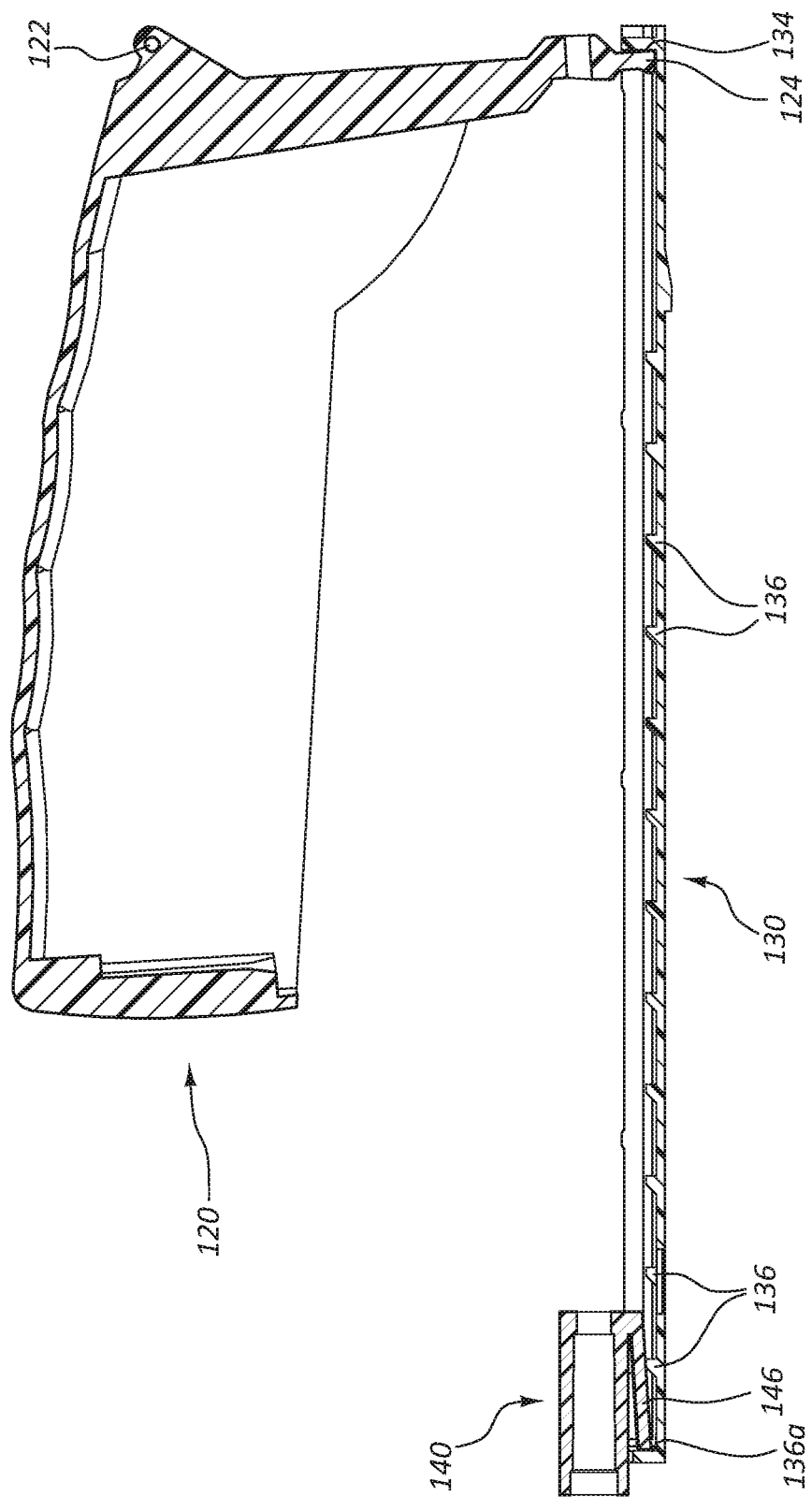
FIG. 5 is a cross-sectional view of another portion of the deployment device shown in FIGS. 1 and 2.

FIG. 5 is a cross-sectional view of a portion of the deployment device 100 shown in FIGS. 1 and 2. Specifically, the actuator 120, ratchet slide 130, and carrier 140 are shown in FIG. 5, in the same relative positions, and along the same cross-sectional plane as in FIG. 2.

Referring to FIGS. 2-5, during depression of the actuator 120 with respect to the housing 110, the actuator 120 rotates around the pin aperture 122. This rotation causes displacement of the ratchet slide engaging portion 124 of the actuator 120. The component of this displacement correlating to proximal displacement of the ratchet slide engaging portion 124 also proximally translates the ratchet slide 130 due to interaction between the ratchet slide engaging portion 124 of the actuator 120 and the actuator engaging opening 134 of the ratchet slide 130. Stated another way, the walls or faces that define the actuator engaging opening 134 may contact the ratchet slide engaging portion 124 such that the ratchet slide 130 is displaced when the actuator 120 is displaced.

Proximal displacement of the ratchet slide 130 also proximally displaces the carrier 140 due to interaction between the carrier engaging ratchet lugs 136 and the ratchet slide engaging arm 146. In the depicted embodiment, a distal surface of the ratchet slide engaging arm 146 is in contact with a proximal face of the distal most carrier engaging ratchet lug 136a. This contact exerts proximal force on the distal surface of the ratchet slide engaging arm 146, displacing the carrier 140 in a proximal direction. Accordingly, the ratchet slide 130 and carrier 140 will move proximally until the actuator 120 reaches the end of the stroke.

Figure 6:
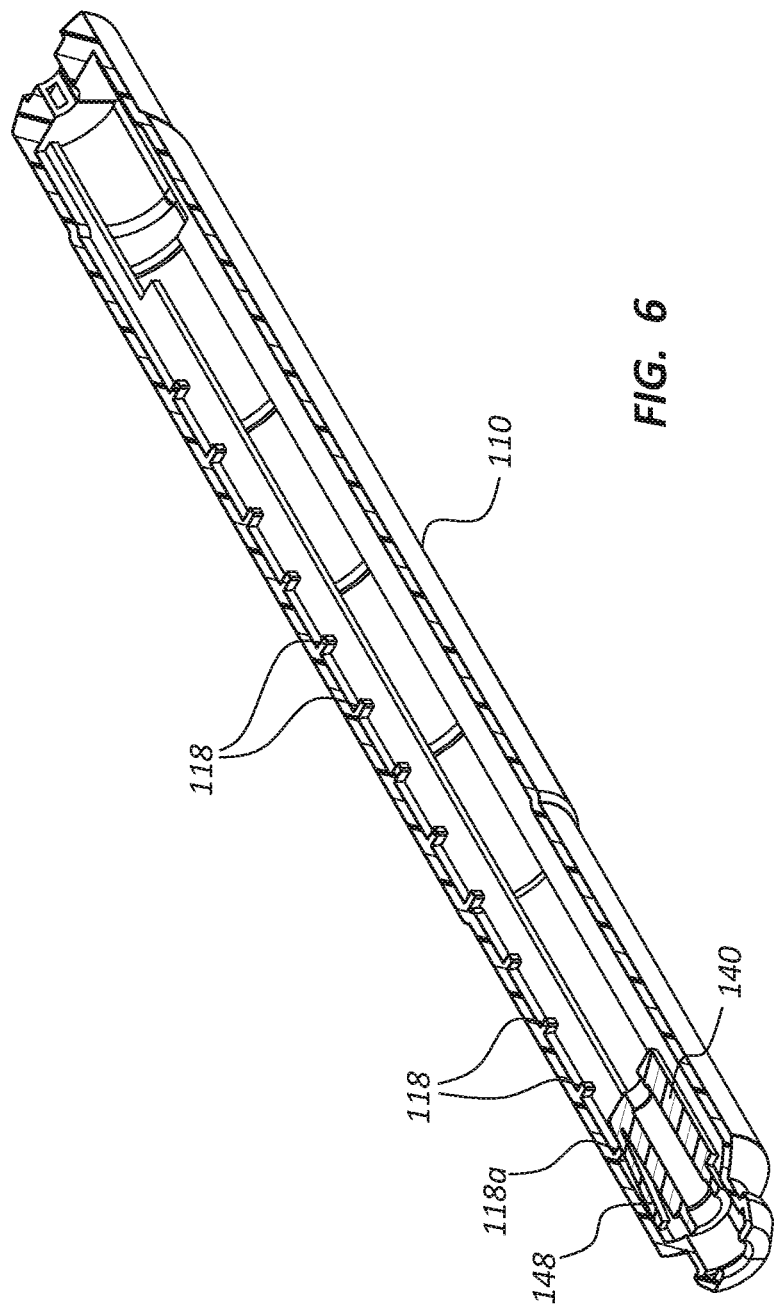
FIG. 6 is a cross-sectional view of yet another portion of the deployment device shown in FIGS. 1 and 2.

FIG. 6 is a cross-sectional view of the housing 110 and the carrier 140 in the same relative positions shown in FIG. 2. The cross-sectional plane of FIG. 6 extends along the longitudinal axis of the deployment device; however, the cross-sectional plane of FIG. 6 extends horizontally, orthogonal to the cross-sectional planes of FIGS. 2, 3B, and 5.

As shown in FIG. 6, the carrier 140 comprises a housing engaging arm 148 extending radially away from a longitudinal axis of the carrier 140. The housing 110 comprises a plurality of carrier engaging housing lugs 118. In FIG. 6, exemplary carrier engaging housing lugs are denoted by reference numeral 118, with the distal most carrier engaging housing lug denoted by reference numeral 118a.

Referring to FIGS. 2-6, as interaction between the actuator 120, ratchet slide 130, and carrier 140 displaces the carrier 140 with respect to the housing 110 (as shown and described above), the housing engaging arm 148 (shown in FIG. 6) of the carrier 140 will deflect radially inward due to contact with one of the carrier engaging housing lugs 118. For example, from the position shown in FIG. 6, as interaction between the distal most carrier engaging ratchet lug 136a and the ratchet slide engaging arm 146 of the carrier 140 draws the carrier 140 proximally, the distal most carrier engaging housing lug 118a causes the housing engaging arm 148 to displace radially inward. The housing engaging arm 148 will continue to deflect radially inward until the distal end of the housing engaging arm 148 is positioned proximal of the distal most carrier engaging housing lug 118a, at which point the housing engaging arm 148 will return to the radially outward configuration shown in FIG. 6. The point at which the housing engaging arm 148 moves proximally of the distal most carrier engaging housing lug 118a, may correspond to the stroke of the actuator 120, such that engagement between the housing engaging arm 148 and the next carrier engaging housing lug 118 (moving in a proximal direction) occurs at the end of the stroke, which may correspond to contact between the ratchet slide 130 and/or actuator 120 and a positive stop on the housing 110 defining the end of the stroke.

As the actuator 120 is released following the stroke, interaction between the spring 115, the housing 110, and the actuator 120 will return the actuator 120 to the unconstrained position (the position shown in FIG. 2) as discussed above. Corresponding rotation of the actuator 120 about the pin aperture 122 will thus correlate to displacement of the ratchet slide engaging portion 124, including a component of displacement in the distal direction. Interaction between the ratchet slide engaging portion 124 and the actuator engaging opening 134 will then correlate to distal displacement of the ratchet slide 130. Thus, when the actuator 120 is released at the end of a stroke, the actuator 120, the spring 115, and the ratchet slide 130 return to the same positions relative to the housing as shown in FIG. 2.

As the actuator 120 returns to the unconstrained position, however, interaction between the housing engaging arm 148 and the carrier engaging housing lug 118 prevents distal displacement of the carrier 140. Specifically, the distal surface of the housing engaging arm 148 will be in contact with a proximal facing surface of a carrier engaging housing lug 118, the interaction preventing the carrier 140 from returning to the pre-stroke position. In the exemplary stroke discussed above, the distal most carrier engaging housing lug 118a displaced the housing engaging arm 148 during the stroke, and the housing engaging arm 148 engaged with the distal most carrier engaging housing lug 118a following the stroke. Subsequent strokes move the carrier 140 along the plurality of carrier engaging housing lugs 118 in a proximal direction.

As the actuator 120 returns to the unconstrained state, radially inward displacement of the ratchet slide engaging arm 146 of the carrier 140 allows the ratchet slide 130 to move distally with respect to the carrier 140, as engagement between the carrier 140 and the carrier engaging housing lugs 118 arrest distal displacement of the carrier 140.

Referring to FIGS. 2-6, with particular reference to the view of FIG. 5, distal displacement of the ratchet slide 130 with respect to the carrier 140 creates interaction between the carrier engaging ratchet lugs 136 and the ratchet slide engaging arm 146 causing the ratchet slide engaging arm 146 to displace radially inward. The proximal facing surface of the carrier engaging ratchet lugs 136 may be angled to facilitate this interaction. In the exemplary stroke discussed above, engagement between the distal most carrier engaging ratchet lug 136a displaced the carrier 140 in a proximal direction; during the return of the actuator 120, the next carrier engaging ratchet lug 136 (in a proximal direction) causes the radially inward displacement of the ratchet slide engaging arm 146 until the ratchet slide engaging arm 146 is proximal of the carrier engaging ratchet lug 136. At that point the ratchet slide engaging arm 146 returns to a radially outward position (analogous to that shown in FIG. 5) though the distal surface of the ratchet slide engaging arm 146 is now engaged with a proximal face of the next carrier engaging ratchet lug 136 (again in a proximal direction). Displacement of the ratchet slide 130 sufficient to move to engagement with a subsequent carrier engaging ratchet lug 136 may correspond with the magnitude of ratchet slide 130 displacement corresponding to a return of the actuator 120. Subsequent returns of the actuator 120 following strokes move the ratchet slide 130 such that the plurality of carrier engaging ratchet lugs 136 may serially engage the carrier 140, stroke after stroke.

Accordingly, as described above, depressing the actuator 120 for a full stroke, then allowing the actuator 120 to return to the unconstrained position, displaces the carrier 140 with respect to the housing 110 in discrete increments, corresponding to the distance between adjacent carrier engaging housing lugs 118 along the longitudinal direction. Interaction of the actuator 120 and positive stops associated with the housing 110, carrier arms (e.g., ratchet slide engaging arm 146 and housing engaging arm 148), and lugs (e.g., carrier engaging housing lugs 118 and carrier engaging ratchet lugs 136) may also combine to give a user tactile and audible feedback as the carrier 140 is incrementally displaced. Further, one or more opening in the housing 110 may allow a user to observe the relative position of the carrier 140 providing further feedback as to carrier 140 position.

As detailed below, the relative position of the carrier 140 with respect to the housing 110 may correlate to the degree of deployment of a stent from the deployment device 100. Thus, visual, audible, and tactile feedback as to the position of the carrier 140 provides a user with information regarding stent deployment during use of the deployment device 100. This information may correlate to increased control during deployment as the practitioner quickly and intuitively can surmise the degree of stent deployment.

As outlined above, tactile and/or audible feedback result from the interactions of the carrier 140, ratchet slide 130, housing 110, and/or actuator 120. For example, as the ratchet slide engaging arm 146 or housing engaging arm 148 of the carrier 140 deflects radially inward then return outward, there may be an audible and/or tactile response.

The device may be configured for visual feedback of, or relating to, the relative deployment of a stent. For example, in some embodiments, the housing 110 may comprise viewing windows to allow a practitioner to observe the position of the carrier 140 relative to the housing 110. Further, indicia on the housing 110 may correlate the position of the carrier 140 to the degree of deployment of a stent.

The increments of displacement of the carrier 140 may correlate to standard stent lengths or units of measure. For example, many stents are sized in 1 cm increments. Configuration of the increments of displacement on the carrier 140 in 1 cm increments would thus directly correlate with stent length at a 1:1 ratio. Any other ratio, including embodiment wherein a stroke correlates to a greater length (such as 2, 3, 4, or 5 cm) or a lesser length (such as 0.01, 0.1, 0.25, 0.5, or 0.75 cm) are likewise within the scope of this disclosure.

In some embodiments, interaction between the carrier 140, the ratchet slide 130, the housing 110, and/or the actuator 120 may comprise additional carrier engaging ratchet lugs 136 and/or carrier engaging housing lugs 118. For example, the carrier engaging ratchet lugs 136 may be spaced to enable semi-continuous ratcheting of the ratchet slide 130 with respect to the actuator 120 and/or the housing 110. Such an embodiment is described in further detail below in reference to the deployment device 400 depicted in FIGS. 14-19.

The deployment device 100 may be configured as a universal device operable with various stent lengths. In some embodiments a practitioner may directly equate the number of strokes needed to deploy a stent with the length of the stent loaded in the deployment device 100 (such as four strokes for a four centimeter stent). Further, a single design of deployment device 100 may be utilized with various lengths of stents, with a maximum length related to the maximum length of travel of the carrier 140.

The nature of depression of the actuator 120 may facilitate one-handed operation and may be ergonomically designed. First, a practitioner need only grip the deployment device with one hand to depress the actuator, leaving a second hand free for other therapy needs. Further, the direction with which the deployment device is gripped, with the practitioner's hand extending laterally away from the longitudinal axis of the deployment device and the lateral direction of depression, as opposed, for example, to longitudinal gripping to actuate, may be ergonomically desirable. Lateral gripping and input may more readily present the deployment device 100 for use when the delivery catheter assembly 104 is disposed within a patient's body, not requiring the practitioner to move to an awkward stance with respect to other therapy tools. Further, the input portion 121 of the actuator 120 may provide additional surface for a practitioner to grip, facilitating use of a greater portion of a practitioner's hand for actuation, as compared to a finger trigger or similar actuation mechanism.

The incremental displacement of the carrier 140 may further facilitate partial deployment of a stent, allowing a practitioner to deploy the stent in increments, potentially adjusting or confirming the position of the stent between these increments.

Still further, the deployment device 100 may be configured for use with either the right or left hand, or gripped with the fingers or palm in contact with the actuator 120 without changing the design of the deployment device 100. These features may further increase user comfort and control. Viewing windows in the housing 110 to confirm the position on the carrier 140 may be located on one or both sides of the housing 110 and may be associated with indicia correlating to stent length or other factors.

Moreover, the relative lengths of the input portion 121 and transfer arm 123 of the actuator 120 may be configured to provide mechanical advantage when deploying a stent. This may increase comfort and control during use. The ratio of the length of the input portion 121—from its distal end to the pin aperture 122—to the length of the transfer arm 123—from the pin aperture 122 to the ratchet slide engaging portion 124—may be greater than or equal to 1.5:1, including 2:1, 2.5:1, 3:1, 3.5:1 or greater. This ratio correlates to the mechanical advantage provided by the device. In some instances the mechanical advantage provided may be 1.5:1, 2:1, 2.5:1, 3:1, 3.5:1 or greater. Stated another way, the ratio of length of travel of the input portion 121 to the corresponding length of travel of the ratchet slide engaging portion 124 may be 1.5:1, 2:1, 2.5:1, 3:1, 3.5:1 or greater. Accordingly, the input force applied against the input portion 121 may result in a greater force exerted by the ratchet slide engaging portion 124 on the ratchet slide 130. The ratio of the force exerted on the ratchet slide 130 to the input force may be 1.5:1, 2:1, 2.5:1, 3:1, 3.5:1 or greater.

Figure 7:
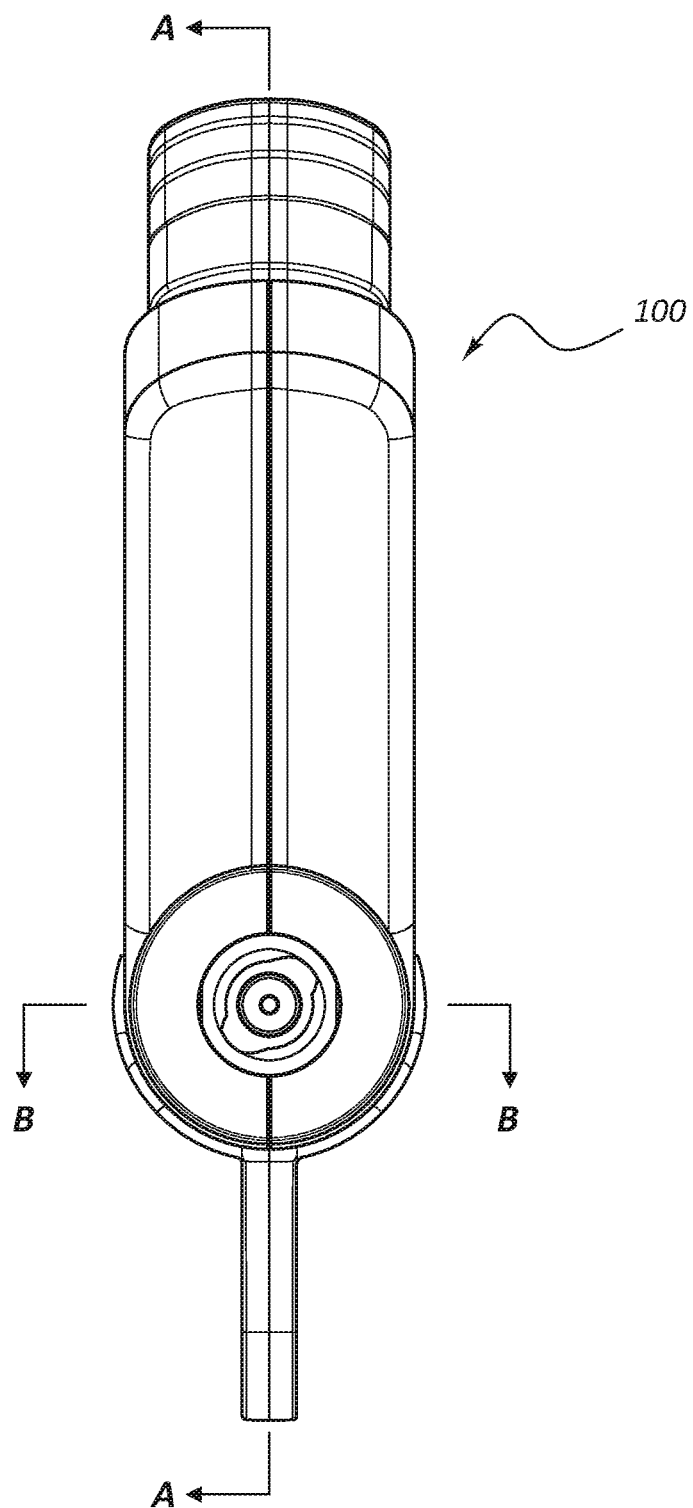
FIG. 7 is a front view of the deployment device of FIG. 1, illustrating certain cross-sectional planes described herein.

FIG. 7 is a front view of the deployment device 100, illustrating two cross-sectional planes. Specifically, plane A-A extends vertically along the longitudinal axis of the deployment device 100 viewing the exposed components in a right to left direction. Plane A-A corresponds to the cross-sectional plane of FIGS. 2, 3B, and 5. Plane B-B also extends from the longitudinal axis of the deployment device 100, though Plane B-B extends horizontally therefrom. Plane B-B corresponds to the cross-sectional plane of FIG. 6, and is viewed from a top to bottom direction. The longitudinal axis of the deployment device 100 is in both planes A-A and B-B, with the line defined as the intersection between these planes being the same line as the longitudinal axis as referenced herein.

Figure 8:
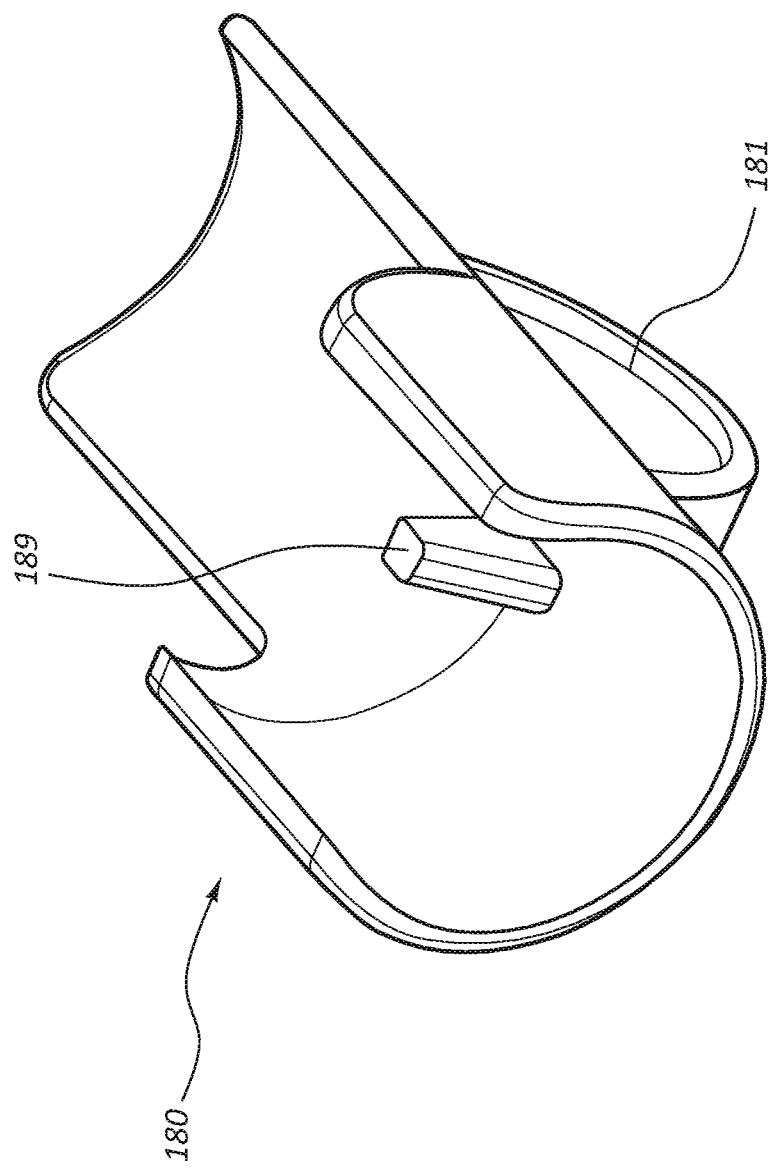
FIG. 8 is a perspective view of the safety member of the deployment device of FIG. 1.

Additionally, as stated above, the deployment device 100 may comprise a safety member 180. FIG. 8 is a perspective view of the safety member 180 of the deployment device 100. The safety member 180 may be configured with a circular or partially circular opening configured to snap onto an outside surface of a portion of the deployment device 100. Referring to both FIG. 2 and FIG. 8, the safety member 180 may comprise a safety lug 189 that extends through a ratchet slide safety opening (139 of FIG. 3A) and a similar safety opening in the housing 110 (not shown). When the safety lug 189 is disposed within these openings, the safety lug 189 may prevent proximal displacement of the carrier 140 and the ratchet slide 130, thus preventing inadvertent deployment of a stent. A practitioner may leave the safety member 180 in place during displacement of the delivery catheter assembly 104 to a treatment region. Due to interactions between the carrier 140, ratchet slide 130, and actuator 120, the safety member 180 likewise prevents displacement of the actuator 120 when the safety lug 189 extends through the openings.

In the depicted embodiment, the safety lug 189 extends through a bottom portion of the housing 110 and ratchet slide 130. In other embodiments, the safety lug 189 may extend through a top surface of the housing 110, interacting with the carrier 140 but not directly with the ratchet slide 130. Nevertheless, prevention of proximal displacement on the carrier 140 only, will also prevent displacement of the ratchet slide 130 and the actuator 120 due to the interaction between these elements.

In some embodiments, the safety member 180 may be tethered to the deployment device 100, or may comprise a sliding switch or other element operably coupled to the housing 110 or other components of the deployment device 100. In the depicted embodiment, the safety member 180 is removably coupled.

Figure 9:
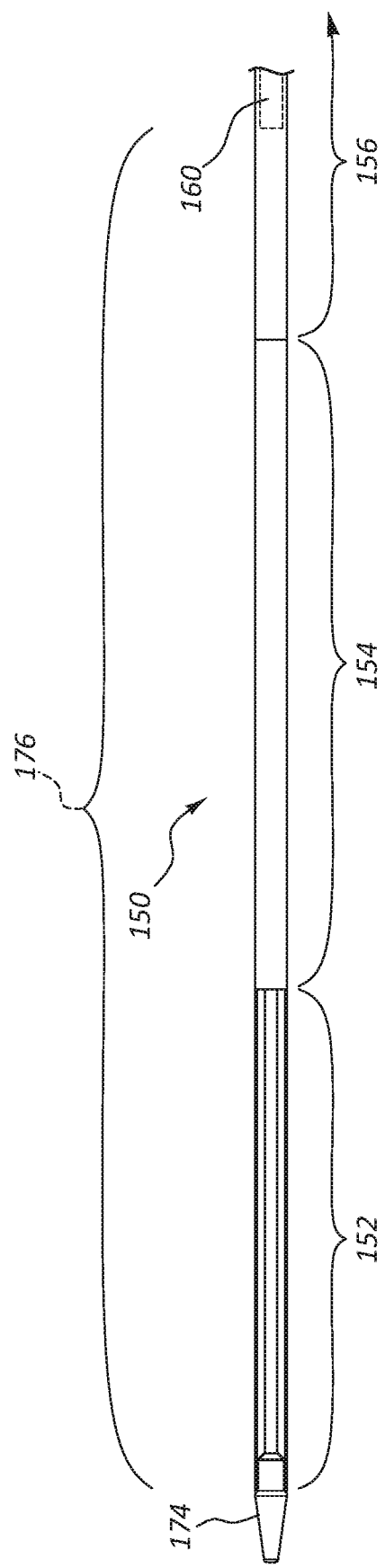
FIG. 9 is a side view of a portion of the delivery catheter assembly of the deployment device of FIG. 1.
Figure 10:
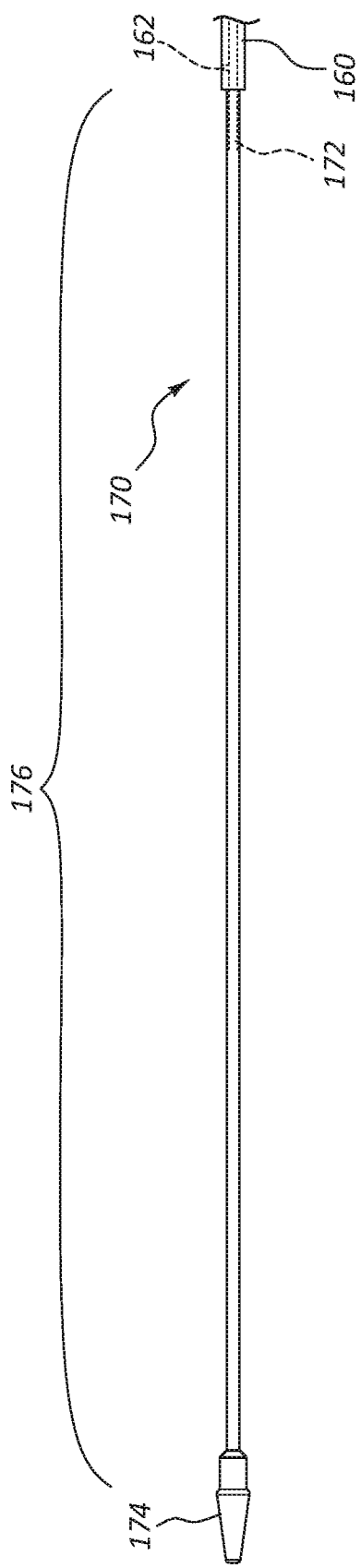
FIG. 10 is a side view of another portion of the delivery catheter assembly of the deployment device of FIG. 1.

FIG. 9 is a side view of a portion of the delivery catheter assembly 104 of the deployment device 100. Specifically, FIG. 9 is a side view of a distal section of the delivery catheter assembly 104. FIG. 10 is a side view of the same longitudinal section of the delivery catheter assembly 104 as shown in FIG. 9; however, the outer sheath (150 of FIG. 9) has been removed to show other components.

Referring to FIGS. 1, 2, 9, and 10, the delivery catheter assembly 104 may be configured to deploy a stent as the deployment device 100 is manipulated, as discussed above. The delivery catheter assembly 104 may comprise an outer sheath 150, extending from the handle assembly 102. The outer sheath 150 may be fixedly coupled to the carrier 140. The delivery catheter assembly 104 may further comprise an intermediate sheath 160 and an inner sheath 170, both disposed within the outer sheath 150, and both fixedly coupled to the housing 110. Thus, proximal displacement of the carrier 140 with respect to the housing 110 will proximally displace the outer sheath 150 with respect to both the intermediate sheath 160 and the inner sheath 170.

The outer sheath 150 may comprise a shaft section 156 extending from the carrier 140 in a distal direction. At the distal end of the shaft section 156 the outer sheath 150 may comprise a flex zone 154 extending from the shaft section 156 in a distal direction. Finally, the outer sheath 150 may comprise a pod 152 extending from the flex zone 154 in a distal direction. (As shown in FIG. 9, the pod 152 may be transparent.)

The shaft section 156 of the outer sheath 150 may have a different stiffness and/or durometer than the flex zone 154 and/or the pod 152. The flexibility toward the distal end of the outersheath 150 may improve trackability of the delivery catheter assembly 104 over a guidewire and may be less traumatic, while a stiffer shaft may be more kink resistant and/or transmit displacement and/or torque along the shaft section 156.

The pod 152 may be configured to retain a crimped or otherwise constrained stent. Removal of the pod 152 from the stent may allow the stent to self-expand, and thereby deploy. It is within the scope of this disclosure for the pod 152 to be any relative length, the flex zone 154 to be any relative length, and the shaft section 156 to be any relative length. Thus, in some instances, a constrained stent may be in one, two, or all three of these portions of the outer sheath 150. For example, in the illustrated embodiment, an annular space 176 (described further below) is configured to receive a crimped stent extending along the pod 152 as well as portions of the flex zone 154 and shaft section 156. In other embodiments, the annular space 176 may correlate just to the pod 152 segment, meaning the device is configured to retain a crimped stent only within the pod 152 segment.

The distal tip 174 of the delivery catheter assembly 104 may be coupled to and/or integrally formed with the inner sheath 170. A lumen 172 may extend along the inner sheath 170 from the proximal end of the deployment device 100 to the distal tip 174. A luer fitting 113 coupled to the housing 110 may be in communication with the lumen 172. A guidewire may thus extend through the luer fitting 113, through the lumen 172, and out of the distal tip 174. Further, fluid introduced into the luer fitting 113 may be utilized to flush the lumen 172.

The inner sheath 170 may be fixed to the housing, for example, at the proximal end of the inner sheath 170. An intermediate sheath 160, also fixed to the housing 110, may extend over a portion of the inner sheath 170. The intermediate sheath 160 and inner sheath 170 may or may not be directly fixed to each other. In some embodiments, the intermediate sheath 160 may be a close slip fit over the inner sheath 170.

The inner sheath 170 extends distally beyond a distal end of the intermediate sheath 160, creating an annular space 176 between the inner sheath 170 and the outer sheath 150 adjacent the distal tip 174, extending proximally to the distal end of the intermediate sheath 160. This annular space 176 may be configured to retain a crimped stent.

As the deployment device 100 is manipulated to incrementally displace the carrier 140 with respect to the housing 110, the outer sheath 150 is incrementally displaced proximally with respect to the inner sheath 170 and intermediate sheath 160. The distal end of the intermediate sheath 160 interacts with the proximal end of the stent, preventing the stent from being drawn back with the outer sheath 150. Thus, the stent is incrementally exposed, and allowed to self-expand and deploy.

In some embodiments, a fluid aperture 162 in the intermediate sheath 160 may extend through the wall of the intermediate sheath 160 and the wall of the inner sheath 170, into fluid communication with the inner lumen 172. This fluid aperture 162 may thus provide fluid communication between the annular space 176 and the inner lumen 172, as fluid within the inner lumen 172 can move through the fluid aperture 162 and into the annular space 176. This communication may be used to flush the annular space 176 during use, which may be configured to remove air or other unwanted materials in the annular space 176 or around the crimped stent.

The distal tip 174 may comprise a flexible material and may be configured to be atraumatic. The distal tip 174 may comprise nylons, including PEBAX® polyether block amides.

In some instances braided or coil reinforcements may be added to the outer sheath 150, the intermediate sheath 160, and/or the inner sheath 170 to increase kink resistance and/or elongation. Reinforcing members may comprise stainless steel, nitinol, or other materials and may be round, flat, rectangular in cross section, and so forth.

One, two, or all of the outer sheath 150, the intermediate sheath 160, and/or the inner sheath 170 may be configured with varying durometers or other properties along the length thereof. In some instances the outer sheath 150 may be configured with a proximal section with a durometer between 72 and 100 on the Shore D scale or may be greater than 100 on the Shore D scale. A second portion of the outer sheath 150 may comprise a durometer of 63 on the Shore D scale, and a distal section with a durometer between 40 and 55 on the Shore D scale. Any of these values, or the limits of any of the ranges, may vary by 15 units in either direction. In some instances the second portion will begin about six inches from the distal end of the outer sheath 150, and the distal section will begin about three inches from the distal end of the outer sheath 150. These sections may or may not correspond to the shaft section 156, the flex zone 154, and the pod 152 as described above. The intermediate sheath 160 may be configured with varying durometer zones within the same ranges of hardness and length.

Any of the inner sheath 170, intermediate sheath 160, and outer sheath 150 may have differing durometer or flex zones along their lengths, and these zones may overlap in various ways to create various stress/strain profiles for the overall delivery catheter assembly 104. Overlapping of such zones may reduce tendency to kink, including tendency to kink at transition zones. Further, the housing 110 may be coupled to a strain relief member 116 (as shown in FIG. 2).

Any of the outer sheath 150, the intermediate sheath 160, and the inner sheath 170 may be comprised of nylons, including PEBAX® polyether block amides. Further, during manufacture, any of these members may be configured with a low friction outer surface, including through "frosting" the materials, by blowing air across the material during extrusion, or by using additives during extrusion to reduce friction.

In some instances, during manufacture the distal tip 174 may be pulled into interference with the outer sheath 150, prestressing the inner sheath 170 in tension. This may reduce any effects of material creep or elongation during sterilization, keeping the distal tip 174 snugly nested with the outer sheath 150. Further, during manufacture, the interface zone between the outer sheath 150 and the carrier 140 may be configured with a tolerance zone, meaning the outer sheath 150 can be coupled to the carrier 140 at multiple points along an inside diameter of the carrier 140. This tolerance may enable manufacturing discrepancies or variations to be taken up during assembly to ensure a snug nest between the distal tip 174 and the outer sheath 150. The same tolerance fit may be applied to the inner sheath 170 and/or the intermediate sheath 160 wherein these members couple to the housing 110, including a fit zone along an inside diameter of the luer fitting 113.

In some instances, the outer sheath 150 may include indicia correlating to the degree to which a stent has been deployed. These indicia may correspond to the position of the outer sheath 150 with respect to the housing 110. For example, as the outer sheath 150 is drawn into the housing 110, different indicia are exposed and/or covered.

Further, in some instances, the deployment device 100 may be configured such that the outer sheath 150 may be distally displaced after the stent is deployed to nest the distal tip 174 in the outer sheath 150 during withdrawal of the deployment device 100 from a patient. Such configurations may include features of the handle assembly 102 that disengage the carrier 140 from one or more elements after stent deployment.

FIGS. 11A-11D depict an embodiment of a deployment device 200 that resembles the deployment device 100 described above in certain respects. Accordingly, like features are designated with like reference numerals, with the leading digits incremented to "2." For example, the embodiment depicted in FIGS. 11A-11D includes a distal tip 274 that may, in some respects, resemble the distal tip 174 of FIGS. 1, 9, and 10. Relevant disclosure set forth above regarding similarly identified features thus may not be repeated hereafter. Moreover, specific features of the deployment device 200 and related components shown in FIGS. 1-10 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the deployment device 200 and related components depicted in FIGS. 11A-11D. Any suitable combination of the features, and variations of the same, described with respect to the deployment device 100 and related components illustrated in FIGS. 1-10, can be employed with the deployment device 200 and related components of FIGS. 11A-11D, and vice versa. This pattern of disclosure applies equally to further embodiments depicted in subsequent figures and described hereafter, wherein the leading digits may be further incremented.

Figure 11A:
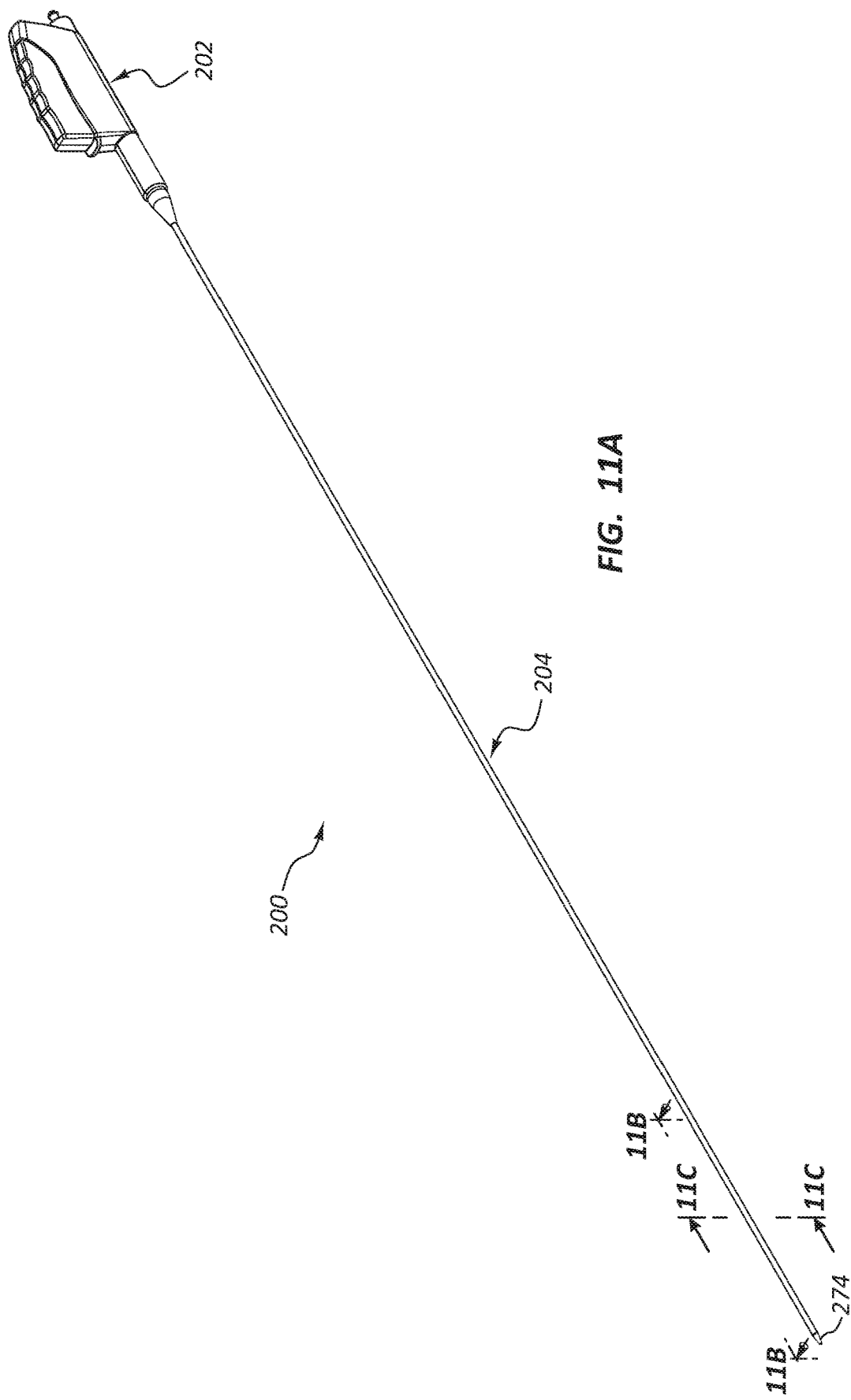
FIG. 11A is a perspective view of another embodiment of a deployment device.

FIG. 11A is a perspective view of the deployment device 200. The deployment device 200 comprises a handle assembly 202 adjacent the proximal end of the deployment device 200. An elongate delivery catheter assembly 204 extends distally from the handle assembly 202 to the distal tip 274. The handle assembly 202 may provide a proximal user input, with one or more components configured to allow a practitioner to deploy or otherwise manipulate a prosthesis disposed within the delivery catheter assembly 204. As discussed above, though specific examples herein may refer to prostheses such as stents, other prostheses are also within the scope of this disclosure, including, but not limited to, vascular prostheses, stents, stent-grafts, shunts, grafts, and so forth.

FIG. 11B is a cross-sectional view of a portion of the delivery catheter assembly 204 of the deployment device 200 of FIG. 11A along plane 11B-11B. Specifically, FIG. 11B is a cross-sectional view of a distal portion of the delivery catheter assembly 204. FIG. 11C is a cross-sectional view of a portion of the delivery catheter assembly 204 of the deployment device 200 of FIG. 11A along plane 11C-11C. FIG. 11D is a side view of the same longitudinal section of the delivery catheter assembly 204 as shown in FIG. 11B; however, the outer sheath (250 of FIG. 11B) has been removed to show other components.

Referring to FIGS. 11B-11D, the delivery catheter assembly 204 may comprise an outer sheath 250. The delivery catheter assembly 204 may further comprise an intermediate sheath 260 and an inner sheath 270, each of which can be disposed within the outer sheath 250. Additionally, the inner sheath 270 can be disposed within the intermediate sheath 260. In certain embodiments, the delivery catheter assembly 204 may lack the intermediate sheath 260. In some embodiments, the outer sheath 250 may be displaced with respect to each of the intermediate sheath 260 and the inner sheath 270.

An annular space 276 may be disposed between each of the outer sheath 250 and the inner sheath 270. In certain embodiments, the annular space 276, or a portion of the annular space 276, may be configured to receive and/or retain a crimped or otherwise constrained stent. Removal or displacement of the outer sheath 250 from around the constrained stent may allow the stent to self-expand, and thereby deploy. It is within the scope of this disclosure for the annular space 276 to be any relative length. Thus, in some instances, a constrained stent may be disposed along only a portion of a length of the annular space 276. In some other instances, a constrained stent may be disposed along substantially the entire length of the annular space 276.

In various embodiments, the intermediate sheath 260 may be directly coupled to the inner sheath 270. In various other embodiments, the intermediate sheath 260 may not be directly coupled to the inner sheath 270. For example, the intermediate sheath 260 may be a close slip fit over the inner sheath 270.

As depicted, the inner sheath 270 can extend distally beyond a distal end of the intermediate sheath 260, creating or forming the annular space 276 between the inner sheath 270 and the outer sheath 250 adjacent the distal tip 274. Furthermore, the annular space 276 may extend proximally from adjacent the distal tip 274 to adjacent the distal end of the intermediate sheath 260. The annular space 276 may be configured to retain a crimped or constrained stent.

A pliant member 290 may partially surround or be disposed around the inner sheath 270. As shown, the pliant member 290 may be disposed around a circumference of the inner sheath 270. For example, the pliant member 290 may be coupled to a portion of an exterior surface of the inner sheath 270. The pliant member 290 may also be disposed within a portion of the annular space 276. In some embodiments, the pliant member 290 may be configured to engage and/or retain a stent or a constrained stent. Stated another way, the pliant member 290 may at least partially grip, anchor, hold, and/or grasp the stent or the constrained stent. In certain embodiments, the stent may be disposed around the pliant member 290 and then the stent may be constrained, crimped, and/or loaded around the pliant member 290. Further, a portion of the loaded stent (e.g., an inner surface of the loaded stent) may imprint within a portion of the pliant member 290 (e.g., an outer surface of the pliant member 290) as discussed in further detail below.

In some embodiments, the pliant member 290 may comprise two or more layers. In certain embodiments, the pliant member 290 may comprise two or more materials. Each of the materials may have different or various properties, for example, variations in thickness, durometer, elasticity, etc. In certain embodiments, the pliant member 290 may comprise an inner layer, wherein the inner layer is configured to adhere to or couple with the inner sheath 270 (e.g., the inner layer may be designed for optimal adhesion to the inner sheath 270). Furthermore, the pliant member 290 may comprise an outer layer, wherein the outer layer is configured to comply or imprint with the stent or the constrained stent. For example, the inner layer of a pliant member may comprise a grafted polyolefin (e.g., OREVAC®), and an outer layer of the pliant member may comprise a thermoplastic elastomer (e.g., CHRONOPRENE™). A portion of the inner sheath 270 may be formed from a polyether block amide (e.g., PEBAX®), and the OREVAC® inner layer can couple with or form a bond with (e.g., a strong bond with) the PEBAX® inner sheath. Stated another way, the OREVAC® may be used as a tie layer between each of the PEBAX® and the CHRONOPRENE™.

In some embodiments, the pliant member 290 may be configured to limit or prevent longitudinal displacement of the constrained stent. For example, the pliant member 290 may grip the constrained stent such that longitudinal displacement of the constrained stent is limited or prevented. In certain embodiments, the pliant member 290 may be configured to limit or prevent the constrained stent from collapsing or accordioning (e.g., longitudinally folding on itself). For example, the pliant member 290 may provide axial support to the constrained stent. Further, the pliant member 290 may be configured to partially surround one or more portions of the constrained stent, meaning that the pliant member 290 may conform to at least a portion of the constrained stent. For example, the pliant member 290 may conform to portions of the inner surface, shape, edges, and/or texture of the constrained stent.

The constrained stent (e.g., the inner surface of the constrained stent) may at least partially imprint around the pliant member 290. In some embodiments, imprinting of a helical stent (e.g., a stent having a helical stent geometry) around the pliant member 290 may support rows of coils of the helical stent. Imprinting of the helical stent around the pliant member 290 may support each row of coils of the helical stent. In some other embodiments, imprinting of a non-helical stent (e.g., a stent having a non-helical stent geometry) around the pliant member 290 may support rows of coils of the non-helical stent. Imprinting of the non-helical stent around the pliant member 290 may support each row of coils of the non-helical stent.

In certain embodiments, the presence of the pliant member 290 may increase the force needed to proximally displace or pull back on the outer sheath 250. For example, disposition of the pliant member 290 and/or a constrained stent within the annular space 276 may cause or form a tighter fit between each of the inner sheath 270 and the outer sheath 250. However, due at least in part to the mechanical advantage that can be provided by the deployment device, as discussed above, the stent can still be readily deployable by a user.

In various embodiments, the delivery catheter assembly 204 may be coupled to a deployment device including an actuator, wherein the actuator is analogous to the actuator 120. The actuator 120 can provide a mechanical advantage to the deployment device. Furthermore, such a mechanical advantage can assist a practitioner in using the deployment device to deploy a stent that is disposed around the pliant member 290.

The pliant member 290 can be formed from one or more materials that are flexible, malleable, moldable, pliable, and/or supple. For example, the pliant member 290 may comprise one or more silicones, polyether block amides (e.g., PEBAX™), thermoplastic elastomers (e.g., CHRONOPRENE™), and/or other suitable materials. As discussed above, the pliant member 290 may be formed from multiple materials (e.g., the pliant member 290 may include two or more layers). The pliant member 290 may be applied to or disposed on the inner sheath 270 using dip, spray, and/or reflow techniques. Other suitable methods of applying or disposing the pliant member 290 onto a surface (e.g., a surface of the inner sheath 270) are also within the scope of this disclosure.

As illustrated, the pliant member 290 can extend longitudinally along a portion of the inner sheath 270 and/or through a portion of the annular space 276. The pliant member 290 may have varying lengths. In some embodiments, the pliant member 290 may extend from adjacent a proximal end of the distal tip 274 to a position adjacent the distal end of the intermediate sheath 260. In some other embodiments, the pliant member 290 may extend along only a portion of a longitudinal distance between each of the proximal end of the distal tip 274 and the distal end of the intermediate sheath 260. As depicted, the distal end of the intermediate sheath can be disposed proximally of the pliant member 290.

The delivery catheter assembly 204 may be configured to receive and/or retain stents having varying lengths. In various embodiments, the pliant member 290 may have a length that is greater than a length of the stent. In various other embodiments, the pliant member 290 may have a length that is substantially equal to the length of the stent. In various other embodiments, the pliant member 290 may have a length that is less than the length of the stent.

In some embodiments, the pliant member 290 can be longitudinally continuous along the length of the stent. For example, the pliant member 290 may extend longitudinally along the entire length of a constrained stent. In certain embodiments, the pliant member 290 can be circumferentially continuous along an inside surface of the stent. For example, the pliant member 290 may extend along the entire inner circumference of a constrained stent.

The pliant member 290 may have varying durometers. In some embodiments, the durometer of the pliant member 290 may be about 10 to about 60 on the Shore A scale, about 15 to about 45 on the Shore A scale, about 20 to about 30 on the Shore A scale, about 23 to about 27 on the Shore A scale, or another suitable durometer. In some other embodiments, the durometer of the pliant member 290 may be about 25 on the Shore A scale.

The pliant member 290 may also a range of wall thicknesses (e.g., the distance from an interior surface of the pliant member 290 to an exterior surface of the pliant member 290). In certain embodiments, the wall thickness of the pliant member 290 may be from about 0.0005 inch to about 0.050 inch, including from about 0.001 inch to about 0.050 inch, or another suitable thickness.

In some embodiments, a compound or drug may be loaded in the pliant member 290 and/or on an outer surface of the pliant member 290. For example, an anticoagulant drug may be loaded in and/or coated on the pliant member 290.

Analogous to the discussion above regarding the distal tip 174, the distal tip 274 of the delivery sheath assembly 204 may be coupled to and/or integrally formed with the inner sheath 270. Furthermore, a lumen 272 may extend along the inner sheath 270 from the proximal end of the deployment device 200 to the distal tip 274.

In certain embodiments, the outer sheath 250 may be displaced or incrementally displaced proximally with respect to each of the inner sheath 270 and the intermediate sheath 260. The distal end of the intermediate sheath 260 can engage or interact with the proximal end of the stent, limiting or preventing the stent from being drawn back with the outer sheath 250. Thus, the stent can be incrementally exposed and allowed to self-expand and deploy.

As discussed above regarding the delivery catheter assembly 104, the outer sheath 250, the intermediate sheath 260, and/or the inner sheath 270 may be configured with varying durometers or other properties along the length thereof.

Figure 13A:
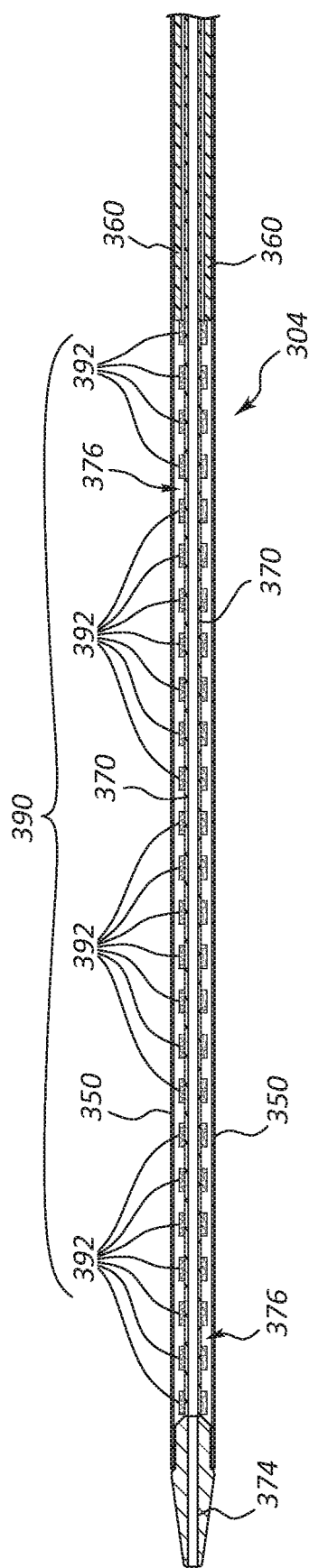
FIG. 13A is a cross-sectional view of a portion of another embodiment of a delivery catheter assembly.
Figure 13B:
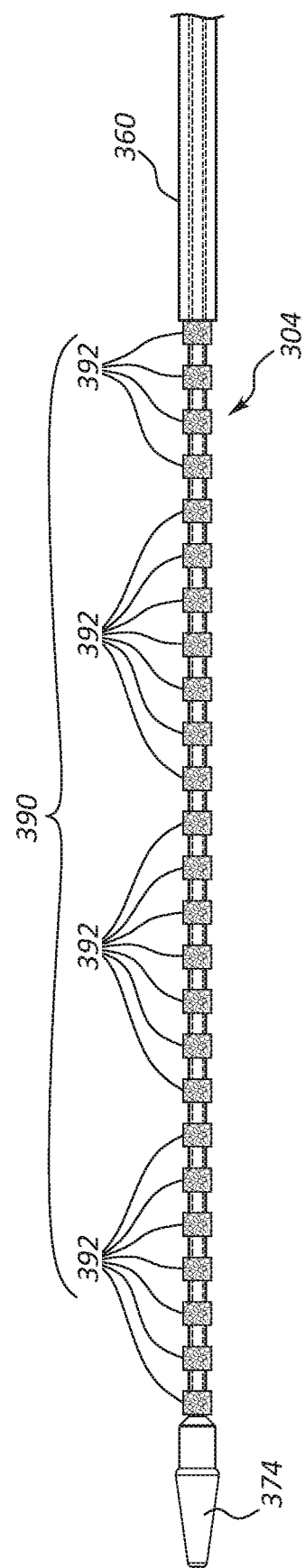
FIG. 13B is a side view of the portion of the delivery catheter assembly of FIG. 13A, wherein an outer sheath has been removed.

FIG. 13A is a cross-sectional view of a portion of another embodiment of a delivery catheter assembly 304. FIG. 13B is a side view of the portion of the delivery catheter assembly 304, wherein an outer sheath (350 of FIG. 13A) has been removed to show other components. As illustrated, a pliant member 390 may include a plurality of annular rings 392. Each of the annular rings 392 can be a discrete or separate annular ring. In some embodiments, the annular rings 392 may be substantially evenly spaced along a portion of a length of an inner sheath 370. In some other embodiments, the annular rings 392 may be spaced in an uneven pattern along a portion of the length of the inner sheath 370. Stated another way, the annular rings 392 may be disposed in an intermittent manner along a portion of the length of the inner sheath 370.

An annular ring 392 can partially surround or be disposed around the inner sheath 370. As shown, each of the annular rings 392 of the pliant member 390 can be disposed around a circumference of the inner sheath 370. For example, each of the annular rings 392 of the pliant member 390 may be coupled to a portion of an exterior surface of the inner sheath 370. In some embodiments, a subset of the annular rings 392 may fully surround the inner sheath 370, and another subset of the annular rings 392 may only partially surround the inner sheath 370.

Each of the annular rings 392 of the pliant member 390 may also be disposed within a portion of an annular space 376. In some embodiments, one or more of the annular rings 392 of the pliant member 390 may be configured to engage and/or retain a stent or a constrained stent. Stated another way, one or more of the annular rings 392 of the pliant member 390 may at least partially grip, anchor, hold, and/or grasp the stent or the constrained stent.

In certain embodiments, the stent may be disposed around a first annular ring 392 disposed to align with a distal end portion of the stent, a second annular ring 392 disposed to align with a middle portion of the stent, and/or a third annular ring 392 disposed to align with a proximal end portion of the stent. In certain other embodiments, a plurality of annular rings 392 may be disposed to align with only one of the distal end portion, the middle portion, or the proximal end portion of the stent. Other configurations (i.e., dispositions) of the one or more annular rings 392 in relation to a stent are also within the scope of this disclosure.

The stent may be constrained, crimped, and/or loaded around the one or more annular rings 392 of the pliant member 390. Further, a portion of the loaded stent (e.g., an inner surface of the loaded stent) may imprint within a portion of the one or more annular rings 392 of the pliant member 390 (e.g., an outer surface of the one or more annular rings 392 of the pliant member 390).

The constrained stent (e.g., the inner surface of the constrained stent) may at least partially imprint around the one or more annular rings 392 of the pliant member 390. In some embodiments, imprinting of a helical stent (e.g., a stent having a helical stent geometry) around the one or more annular rings 392 of the pliant member 390 may support rows of coils of the helical stent. Imprinting of the helical stent around the one or more annular rings 392 of the pliant member 390 may support each row of coils of the helical stent. In some other embodiments, imprinting of a non-helical stent (e.g., a stent having a non-helical stent geometry) around the one or more annular rings 392 of the pliant member 390 may support rows of coils of the non-helical stent. Imprinting of the non-helical stent around the one or more annular rings 392 of the pliant member 390 may support each row of coils of the non-helical stent.

As illustrated, the plurality of annular rings 392 of the pliant member 390 can extend longitudinally along a portion of the inner sheath 370 and/or through a portion of the annular space 376 (i.e., from the proximal-most annular ring 392 to the distal-most annular ring 392). In some embodiments, the plurality of annular rings 392 of the pliant member 390 may extend from adjacent a proximal end of a distal tip 374 to a position adjacent the distal end of an intermediate sheath 360. In some other embodiments, the plurality of annular rings 392 of the pliant member 390 may extend along only a portion of a longitudinal distance between each of the proximal end of the distal tip 374 and the distal end of the intermediate sheath 360. As depicted, the distal end of the intermediate sheath 360 can be disposed proximally of the plurality of annular rings 392 of the pliant member 390.

The delivery catheter assembly 304 may be configured to receive and/or retain stents having varying lengths. In various embodiments, the plurality of annular rings 392 of the pliant member 390 may have a length that is greater than a length of the stent (i.e., the length from the proximal-most annular ring 392 to the distal-most annular ring 392). In various other embodiments, the plurality of annular rings 392 of the pliant member 390 may have a length that is substantially equal to the length of the stent. In various other embodiments, the plurality of annular rings 392 of the pliant member 390 may have a length that is less than the length of the stent.

Figure 12A:
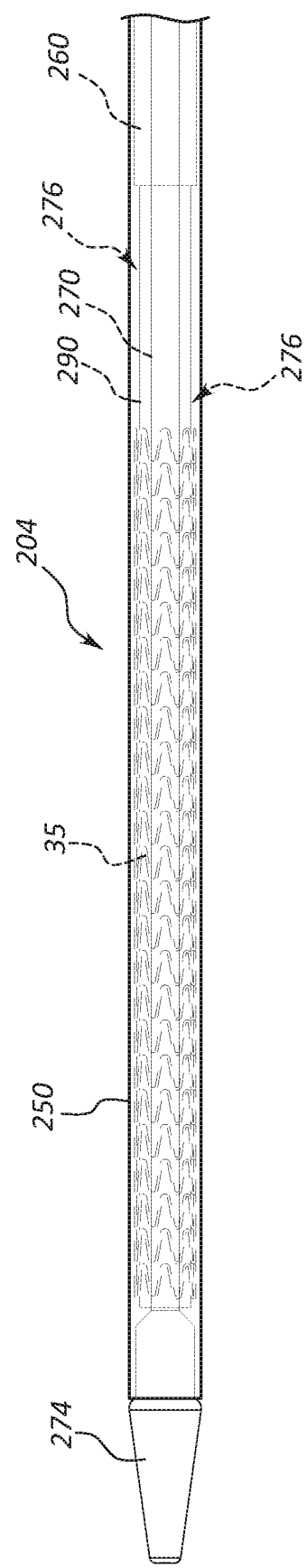
FIG. 12A is a side view of yet another portion of the delivery catheter assembly of the deployment device of FIG. 11A with a prosthesis in a first state.
Figure 12B:
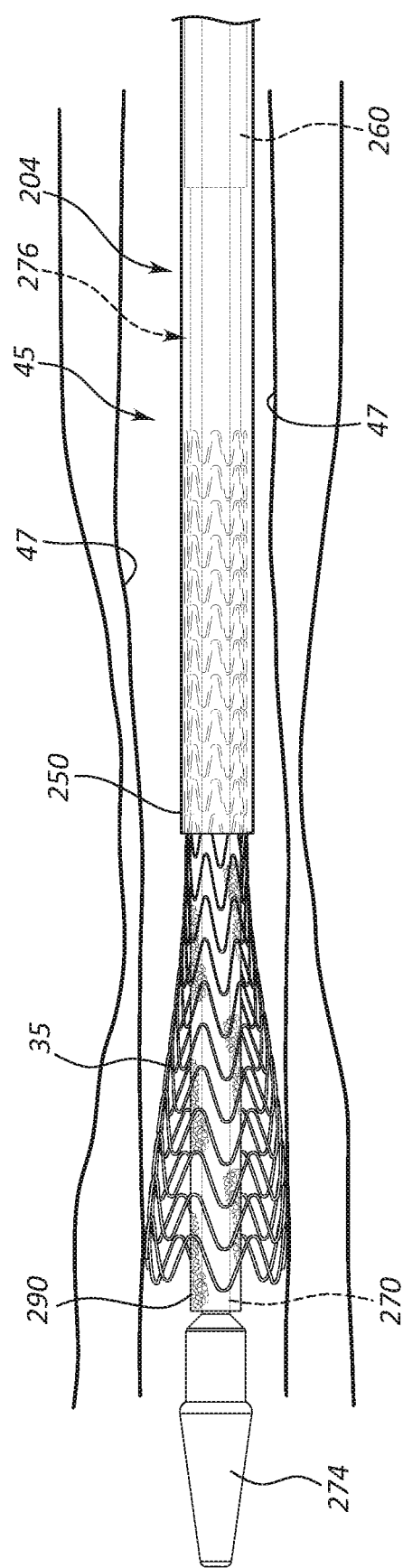
FIG. 12B is a side view of the portion of the delivery catheter assembly of FIG. 12A in a second state.
Figure 12C:
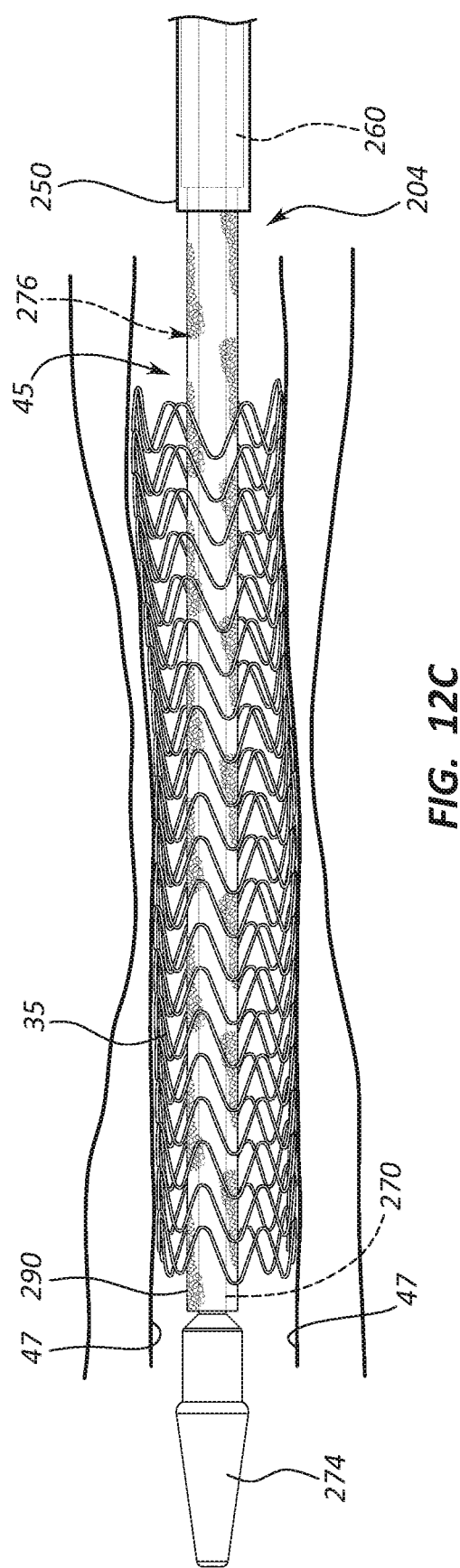
FIG. 12C is a side view of the portion of the delivery catheter assembly of FIG. 12A in a third state.

FIG. 12A is a side view of the distal portion of the delivery catheter assembly 204 of the deployment device 200 of FIG. 11A in a first state. FIGS. 12B and 12C are side views of the distal portion of the delivery catheter assembly 204 in a second state and a third state, respectively.

With reference to FIG. 12A, a stent 35 may be constrained, crimped, or disposed around the pliant member 290 and/or within the annular space 276. In the first state, as illustrated, the outer sheath 250 may be disposed over the stent 35 such that the stent 35 is in a constrained configuration. The constrained stent 35 can extend from the proximal end of the distal tip 274 along only a portion of the pliant member 290, such that a gap or space is present along the pliant member 290 (e.g., between a proximal end of the constrained stent 35 and the distal end of the intermediate sheath 260). In some embodiments, the constrained stent 35 may extend along substantially an entire length of the pliant member 290. In some other embodiments, the constrained stent 35 may be longer than the pliant member 290. For example, in some instances, only a portion of the constrained stent 35 is disposed in the pliant member 290.

FIG. 12B depicts the distal portion of the delivery catheter assembly 204 in the second state. As illustrated, the distal portion of the delivery catheter assembly 204 can be disposed within a vessel 45 (e.g., a vessel of a patient). To deploy the stent 35, the outer sheath 250 may be displaced proximally in relationship to the intermediate sheath 260, the inner sheath 270, and/or the pliant member 290. For clarity, the pattern depicted on the pliant member 290 in FIGS. 12B and 12C differs in certain respects, for example, from the pattern depicted on the pliant member 290 in FIG. 11D. The disclosure herein directed to the pliant member 290 of FIGS. 12B and 12C, however, is relevant to the pliant member 290 of FIG. 11D, and vice versa. In some embodiments, the outer sheath 250, the intermediate sheath 260, and/or the inner sheath 270 may be operably coupled to an actuator, as discussed above in reference to deployment device 100. In some other embodiments, the outer sheath 250, the intermediate sheath 260, and/or the inner sheath 270 may be operably coupled to a housing, as discussed above in reference to deployment device 100, and the housing may be operably coupled to the actuator.

Furthermore, displacement of the actuator may be configured to displace the outer sheath 250 relative to the inner sheath 270 and/or the intermediate sheath 260. As noted above, some embodiments of the delivery catheter assembly 204 may lack an intermediate sheath 260. Proximal displacement of the outer sheath 250 may expose a portion of the constrained stent 35, and as such the stent 35 may at least partially deploy. For example, as portions of the pliant member 290 and the constrained stent 35 are disposed distally of the distal end of the outer sheath 250, a distal portion of the stent 35 may expand radially away from the pliant member 290 and partially deploy.

In certain embodiments, as noted above, the deployment device and/or the actuator may be configured to incrementally deploy the stent 35. For example, the outer sheath 250 may be configured to be proximally displaced relative to the inner sheath 270, the pliant member 290, and the constrained stent 35 in a step-wise or incremental manner. In various embodiments, the pliant member 290 may aid or enhance the deployment of the stent 35. For example, the pliant member 290 may limit or prevent over-deployment of the stent 35 (e.g., "jumping" of the stent 35 out of the delivery catheter assembly 204 and/or jumping of the stent 35 off of the inner sheath 270) during deployment of the stent 35. Further, the pliant member 290 may enhance the accuracy of the deployment of the stent 35, for example, by limiting or preventing over-deployment or jumping of the stent.

In certain embodiments, the pliant member 290 may grip or support a constrained portion of the stent 35 such that the deployed portion of the stent 35 can be pushed and/or shortened during deployment of the stent 35. For example, the delivery catheter assembly 204 and/or the deployment device 200 may be moved or manipulated such that a portion of the stent 35, which is at least partially disposed in the pliant member 290, can be pushed and/or shortened during deployment of the stent 35.

In some embodiments, the delivery catheter assembly 204 may be configured to adjust a length of the stent 35 (e.g., the stent 35 may be shortened) during deployment of the stent 35 such that a user may select a length of the stent 35 (e.g., a custom length of the stent 35) based on a characteristic such as patient anatomy. In certain embodiments, the delivery catheter assembly 204 may have sufficient rigidity and/or deployment control such that a user may push and/or pull the stent 35 to control or determine the length of the stent 35 during deployment of the stent 35. In various embodiments, the pliant member 290 may be configured such that the stent 35 can remain in communication (e.g., direct, physical communication) with the delivery catheter assembly 204 and/or the deployment device 200 for the majority of the deployment of the stent 35.

In some embodiments, the stent may be configured to allow or permit nesting and/or telescoping of the rows of the stent. For example, the stent may comprise a plurality of rows, wherein each row of the plurality of rows is configured to be disposed around at least a portion of an outer surface of an adjacent row. Such a configuration may provide a stent wherein an effective length of the stent can be adjusted during deployment of the stent by a user.

Upon deployment of a portion of the stent 35, the stent 35 (e.g., the distal end of the stent 35) can be disposed against or engaged with a wall 47 of the vessel 45 (see, e.g., FIG. 12B). Pushing or pulling on the stent 35 via the deployment device 200 can compress the stent 35 (i.e., reduce the distance between the coils of the stent 35) and/or stretch the stent 35 (i.e., increase the distance between the coils of the stent 35) along a portion of the stent 35 that is deployed but that is not engaged with the wall 47. During such length adjustments, at least a portion of the non-deployed portion of the stent 35 may be engaged by the pliant member 290. Such a configuration can provide a practitioner with enhanced flexibility during deployment of the stent 35. For example, the practitioner can make adjustments (e.g., small adjustments) to the length of the stent 35, for example, at or around branch vessels or other structures within a patient. Without the pliant member 290, the stent 35 may collapse or accordion within the delivery catheter assembly 204 and/or the annular space 276 during an attempted length adjustment as described above.

FIG. 12C depicts the delivery catheter assembly 204 in the third state, wherein the distal end of the outer sheath 250 has been proximally displaced relative to the proximal end of the stent 35. Accordingly, in the third state the stent 35 may fully deploy within the vessel 45. In some embodiments, the stent 35 may deploy such that it engages or interacts with the wall 47 of the vessel 45.

Methods of preparing or loading a deployment device 200 are disclosed herein. In some embodiments, the methods of preparing the deployment device 200 can include obtaining a delivery catheter assembly 204. The delivery catheter assembly 204 can include an outer sheath 250 and an inner sheath 270, wherein the inner sheath 270 is disposed within the outer sheath 250.

In certain embodiments, the delivery catheter assembly 204 may further include an intermediate sheath 260, wherein the intermediate sheath 260 is disposed between the outer sheath 250 and the inner sheath 260. Additionally, a distal end of the intermediate sheath 260 may be disposed proximally of the distal end of the outer sheath 250 and the distal end of the inner sheath 270.

In various embodiments, the methods of preparing the deployment device 200 may include applying a pliant member 290 on at least a portion of the inner sheath 270. For example, the pliant member 290 may be applied onto an outer surface of the inner sheath 250, and the pliant member 290 may be coupled to the inner sheath 270. The pliant member 290 may be applied to the inner sheath 270 by at least one of dipping, spraying, extrusion, reflowing, or another suitable technique.

As described above, the pliant member 290 may be configured to engage and/or retain a stent 35. Furthermore, a stent 35 may be disposed or positioned around at least a portion of the pliant member 290, and the stent 35 may be constrained, crimped, or loaded within the pliant member 290.

The methods of preparing the deployment device 200 may further include disposing the outer sheath 250 over a portion of the stent 35. Such a configuration of the outer sheath 50 in relation to the stent 35 may aid in constraining the stent 35 within the pliant member 290. When the stent 35 is in the constrained configuration, a distal end of the intermediate sheath 260 may be disposed proximally of a proximal end of the pliant member 290.

Methods of deploying a stent 35 are also provided. In some embodiments, a delivery catheter assembly 204 may be obtained. The delivery catheter assembly 204 may comprise an outer sheath 250, an intermediate sheath 260, and an inner sheath 270. Furthermore, a pliant member 290 can surround a portion of the inner sheath 270. The methods of deploying the stent 35 may include positioning the stent 35 around the pliant member 290 and/or constraining the stent 35 within the pliant member 290. In various embodiments, the outer sheath 250 may also be disposed over the stent 35 (e.g., such that the stent 35 is constrained within a portion of the pliant member 290).

In certain embodiments, methods of deploying the stent 35 may further include displacing an actuator, for example, an actuator that is operably coupled to the delivery catheter assembly 204. Displacement of the actuator can be configured to proximally displace the outer sheath 250 relative to each of the pliant member 290 and the constrained stent 35 such that the stent 35 is partially deployed. As described above, the actuator may be configured to incrementally deploy the stent 35. Accordingly, methods of deploying the stent 35 can also include adjusting the position of the partially deployed stent 35 after each displacement of the actuator. The actuator can be displaced and/or the position of the stent 35 adjusted until the stent 35 is fully deployed. As can be appreciated, each of the methods provided herein can also be adapted for use with the deployment device 100 and the components thereof.

Figure 14:
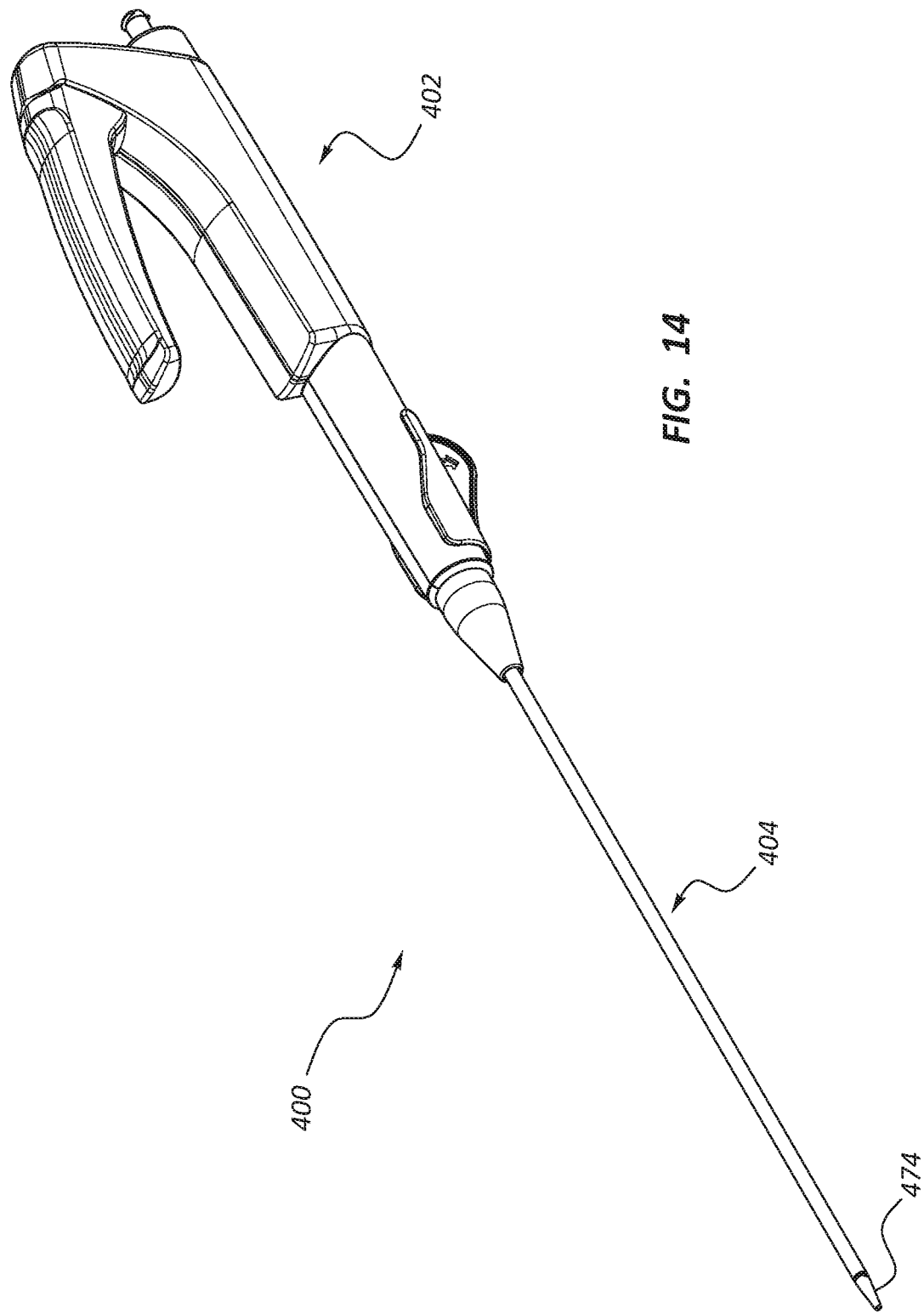
FIG. 14 is a perspective view of another embodiment of a deployment device.

FIG. 14 is a perspective view of a deployment device 400. The deployment device 400 comprises a handle assembly 402 adjacent the proximal end of the deployment device 400. An elongate delivery catheter assembly 404 extends distally from the handle assembly 402 to a distal tip or delivery tip 474. The handle assembly 402 may provide a proximal user input, with one or more components configured to allow a practitioner to deploy or otherwise manipulate a stent disposed within the delivery catheter assembly 404.

As discussed above in reference to the deployment device 100, while in use, the handle assembly 402 may be disposed outside of a patient's body, while the delivery catheter assembly 404 is advanced to a treatment location within the patient's body. As detailed below, a stent may be disposed within a portion of the delivery catheter assembly 404 such that a practitioner may deploy the stent from a distal end of the delivery catheter assembly 404 through manipulation of one or more components of the handle assembly 402.

Figure 15:
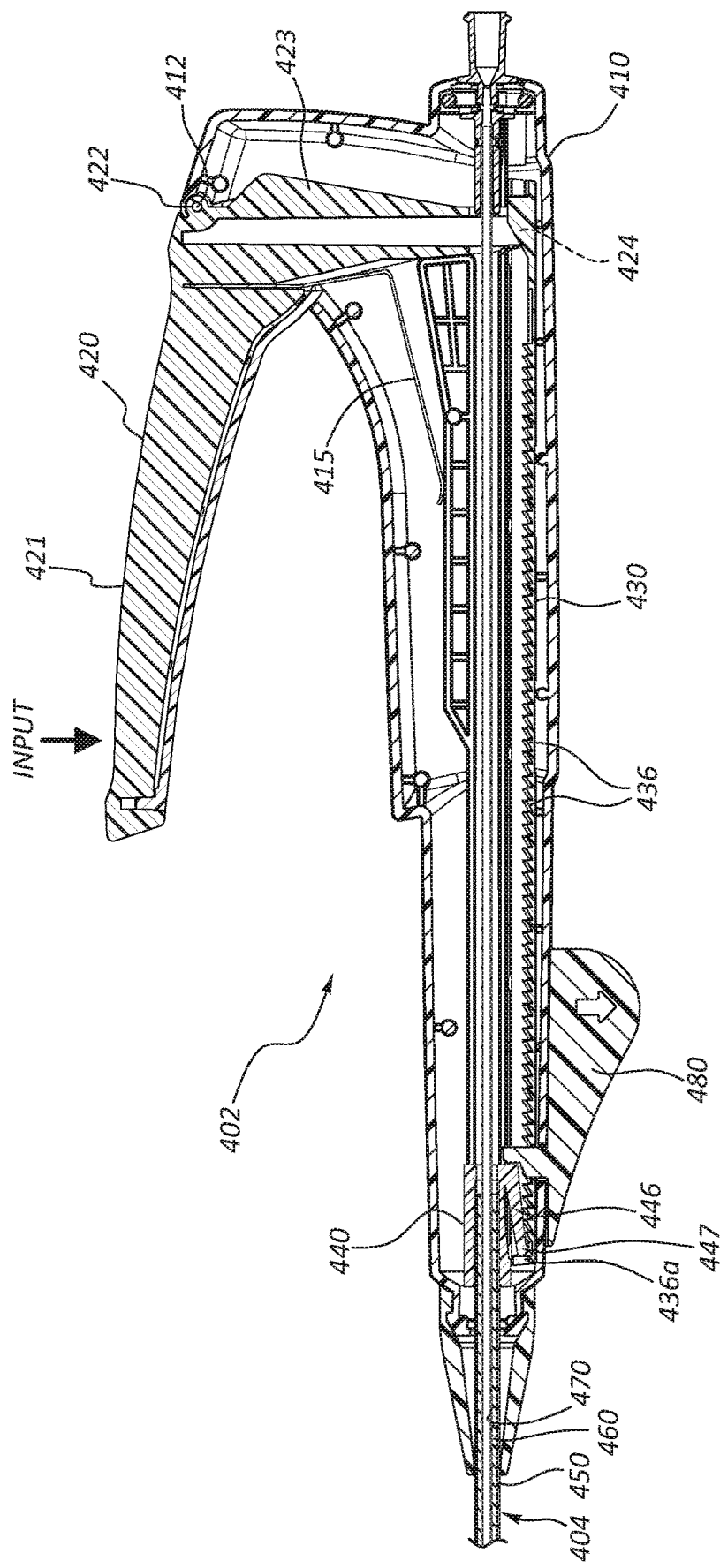
FIG. 15 is a cross-sectional view of a portion of the deployment device of FIG. 14.

FIG. 15 is a cross-sectional view of a portion of the deployment device 400 of FIG. 14. Specifically, FIG. 15 is a side view of a portion of the deployment device 400 of FIG. 14, taken through a cross-sectional plane extending vertically and intersecting a longitudinal axis of the deployment device 400, when the deployment device 400 is positioned as shown in FIG. 14. The longitudinal axis of the deployment device 400 extends along the center of the delivery catheter assembly 404, including along the center of components of the delivery catheter assembly 404 which overlap with the handle 402 assembly, such as an intermediate sheath 460, as shown in FIG. 15.

As the handle assembly 402 is configured to be grasped or otherwise manipulated by a user and the delivery catheter assembly 404 is configured to extend to a treatment location within a patient's body, along the longitudinal axis, the delivery catheter assembly 404 extends in a distal direction away from the handle assembly 402. The proximal direction is opposite, correlating to a direction defined along the longitudinal axis, extending from the distal tip 474 toward the handle assembly 402.

FIG. 15 depicts various internal components of the handle assembly 402, exposed by the cross-sectional view. A portion of the delivery catheter assembly 404 is also shown extending from the handle assembly 402. The handle assembly 402 comprises a housing 410. The housing 410 surrounds certain components of the handle assembly 402, as shown, providing a grip surface for a practitioner.

The actuator 420 is operably coupled to the housing 410. Manipulation of the actuator 420 with respect to the housing 410 may be configured to deploy the stent, as further detailed below. In the depicted embodiment, the actuator 420 is rotatably coupled to the housing 410 by a pin 412. The pin 412 extends from the housing 410 and may be integrally formed with one or more other portions of the housing 410. As shown, the pin 412 extends through a pin aperture 422 in the actuator 420. As discussed above in reference to the actuator 120 and the housing 110, other arrangements for operably coupling the actuator 420 and the housing 410 are also within the scope of this disclosure.

The actuator 420 comprises an input portion 421 extending from the pin aperture 422. In the depicted embodiment, the input portion 421 comprises a surface, at least partially exposed with respect to the housing 410. In operation, a user may manipulate the actuator 420 by exerting a force on the input portion 421, illustrated by the arrow labeled "input" in FIG. 15, displacing the input portion 421 generally toward the longitudinal axis of the deployment device (400 of FIG. 14) and causing the actuator 420 to rotate about the pin 412 with respect to the housing 410. Displacement of the actuator 420 due to a force such as illustrated by the arrow labeled "input" corresponds to "depression" of the actuator 420 or "depression of the actuator 420 with respect to the housing 410."

The actuator 420 may further comprise a transfer arm 423 extending from the pin aperture 422. The transfer arm 423 may be rigidly coupled to the input portion 421, including embodiments wherein both the transfer arm 423 and the input portion 421 are integrally formed with the rest of the actuator 420. The transfer arm 423 extends to a ratchet slide engaging portion 424. Depression of the input portion 421, in the direction shown by the arrow labeled "input," displaces the transfer arm 423 as the actuator 420 is rotated about the pin 412.

Depression of the input portion 421 thus causes displacement of the ratchet slide engaging portion 424 with respect to the housing 410. This displacement of the ratchet slide engaging portion 424 can be understood as rotation about the pin 412 having a proximal translation component and a vertical translation component, as rotation of the input portion 421 in the direction indicated by the arrow labeled "input" will displace (with respect to the housing 410) the ratchet slide engaging portion 424 both proximally and vertically.

A spring 415 may be disposed between the actuator 420 and the housing 410. The spring 415 may be configured to resist displacement of the actuator 420 in the direction indicated by the arrow labeled "input" and may be configured to return the actuator 420 to the relative position shown in FIG. 15 after it has been depressed by a user. When the handle assembly 402 is unconstrained, the spring 415 may thus maintain (or return to) the relative position of the actuator 420 with respect to the handle 410 as shown in FIG. 15.

As the actuator 420 is depressed with respect to the housing 410, the spring 415 compresses and the ratchet slide engaging portion 424 is displaced as described above. Again, the displacement of the ratchet slide engaging portion 424 with respect to the housing 410 can be understood as having a proximal component and a vertical component.

The ratchet slide engaging portion 424 may be operably coupled to a ratchet slide 430 such that displacement of the ratchet slide engaging portion 424 likewise displaces the ratchet slide 430. The ratchet slide 430 may be constrained such that the ratchet slide 430 is configured only for proximal or distal displacement with respect to the housing 410. Thus, operable coupling of the ratchet slide engaging portion 424 to the ratchet slide 430 may allow for sliding interaction between the ratchet slide engaging portion 424 and the ratchet slide 430 such that only the proximal or distal component of the displacement of the ratchet slide engaging portion 424 is transferred to the ratchet slide 430. Stated another way, the ratchet slide 430 may be displaced in a direction parallel to the longitudinal axis of the deployment device 400 while the input displacement may be at an angle to the longitudinal axis of the deployment device 400. It is noted that, in the configuration shown in FIG. 15, a safety member 480 (similar to the safety member 180) may prevent proximal displacement of the ratchet slide 430. Discussion herein relating to displacement of the ratchet slide 430 and related components may thus be understood as disclosure relevant to a configuration of the handle assembly 402 in which the safety member 480 has been removed.

As the actuator 420 is depressed with respect to the housing 410, the ratchet slide 430 may thus be proximally displaced with respect to the housing 410. One or both of the ratchet slide 430 and actuator 420 may also interact with the housing 410 such that there is a positive stop to arrest the depression of the actuator 420 and/or proximal displacement of the ratchet slide 430. This positive stop may be an engaging ledge, shoulder, lug, detent, or other feature coupled to the housing 410, including features integrally formed on the housing 410. As depicted, the positive stop can be disposed proximally of a proximal end of the ratchet slide 430. For example, the proximal end of the ratchet slide 430 can interact with a portion of the housing 410 (e.g., a ledge, shoulder, etc.) disposed proximally of the proximal end of the ratchet slide 430. Accordingly, the handle assembly 402 may be configured such that the ratchet slide 430 is displaced or "travels" as much as possible during depression of the actuator 420.

A full stroke of the actuator 420 may thus correspond to displacement from the unconstrained position shown in FIG. 15, to the positive stop caused by interaction with the housing 410 when the actuator 420 is depressed. A partial stroke of the actuator 420 may correspond to displacement from the unconstrained position shown in FIG. 15, to each and/or any position prior to the positive stop caused by interaction with the housing 410 when the actuator 420 is depressed. Release of the actuator 420 following a full stroke or a partial stroke may then result in a return of the actuator 420 to the unconstrained state, due to the biasing force provided by the spring 415. The unconstrained state shown in FIG. 15 refers to lack of constraint due to user input. In this state, the spring 415 may be partially compressed, and interaction between the actuator 420 and the housing 410 may prevent rotation of the actuator 420 about the pin 412 in the opposite direction to depression of the actuator 420, or the return direction. In other words, interaction between the actuator 420 and the housing 410 (or features of the housing 410) may create a positive stop to the return motion of the actuator 420 as well.

With continued reference to FIG. 15, the ratchet slide 430 may thus be proximally displaced during depression of the actuator 420. Again, such displacement may correspond to a configuration in which the safety member 480 has been removed. Proximal displacement of the ratchet slide 430 may also proximally displace a carrier 440 due to interaction between one or more carrier engaging ratchet lugs 436 on the ratchet slide 430 and a ratchet slide engaging arm 446 coupled to the carrier 440. In some embodiments, the carrier 440 may be coupled to an outer sheath 450. For example, the carrier 440 may be fixedly and/or rigidly coupled to the outer sheath 450. In certain embodiments, an inner sheath 470 may be coupled to the handle assembly 402. For example, the inner sheath 470 may be fixedly and/or rigidly coupled to the handle assembly 402.

Figure 16A:
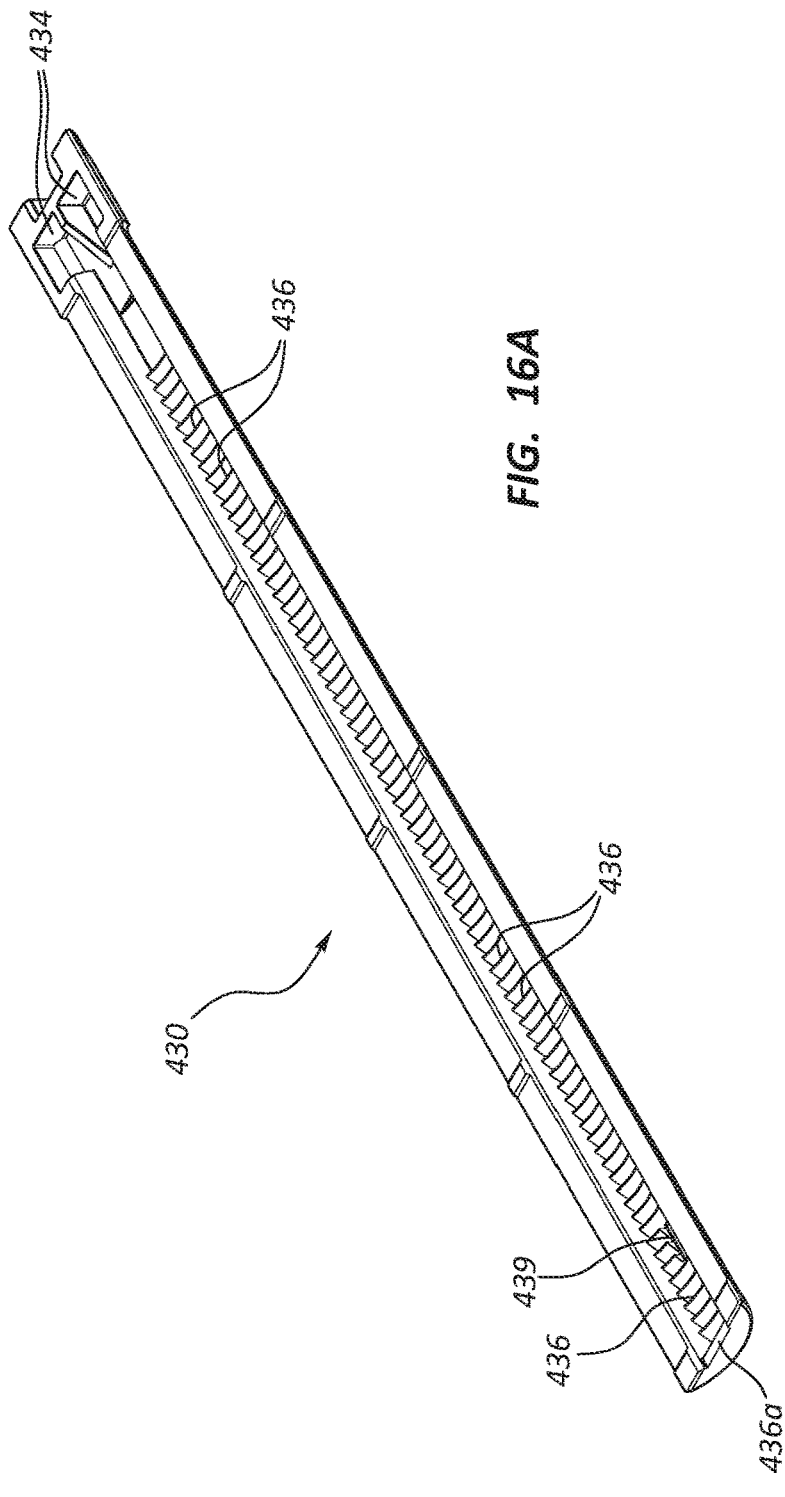
FIG. 16A is a perspective view of a ratchet slide component of the deployment device of FIGS. 14 and 15.
Figure 16B:
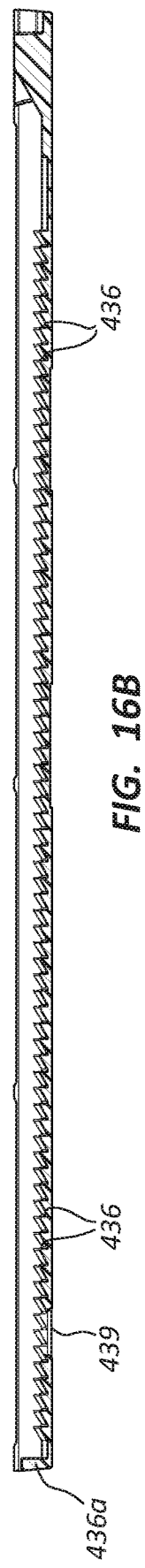
FIG. 16B is a cross-sectional view of the ratchet slide of FIG. 16A.

FIG. 16A is a perspective view of the ratchet slide 430 of the deployment device 400 of FIGS. 14 and 15. FIG. 16B is a cross-sectional view of the ratchet slide 430 of FIG. 16A, taken through a vertical plane disposed along a longitudinal centerline of the ratchet slide 430. When the ratchet slide 430 is disposed within the handle assembly 402 of FIG. 15, this cross-sectional plane would intersect the longitudinal axis of the deployment device 400.

As shown in FIGS. 15, 16A, and 16B, the ratchet slide 430 may comprise a plurality of carrier engaging ratchet lugs 436. The carrier engaging ratchet lugs 436 may be spaced at even intervals along the longitudinal direction of the ratchet slide 430. As depicted, the plurality of carrier engaging ratchet lugs 436 may be disposed semi-continuously. For example, consecutive carrier engaging ratchet lugs 436 may be spaced about 5 mm or less from each other, about 4 mm or less from each other, about 3 mm or less from each other, about 2 mm or less from each other, about 1 mm or less from each other, or any other suitable distance from each other. In the figures, exemplary carrier engaging ratchet lugs are denoted with reference numeral 436, while the distal most carrier engaging ratchet lug, disposed at the distal end of the ratchet slide 430, is denoted with reference numeral 436a.

The ratchet slide 430 further comprises a ratchet slide safety opening 439 (similar to the ratchet slide safety opening 139). The ratchet slide 430 can further comprise an actuator engaging opening 434, which is discussed in more detail below.

As noted above, interaction between the ratchet slide engaging portion 424 of the actuator 420 and the ratchet slide 430 may proximally displace the ratchet slide 430 with respect to the housing 410. Engagement between the carrier 440 and one of the carrier engaging ratchet lugs 436 may also proximally displace the carrier 440 as the ratchet slide 430 is proximally displaced with respect to the housing 410. In the configuration of FIG. 15, the ratchet slide engaging arm 446 of the carrier 440 is engaged with the distal most carrier engaging ratchet lug 436a.

Figure 17:
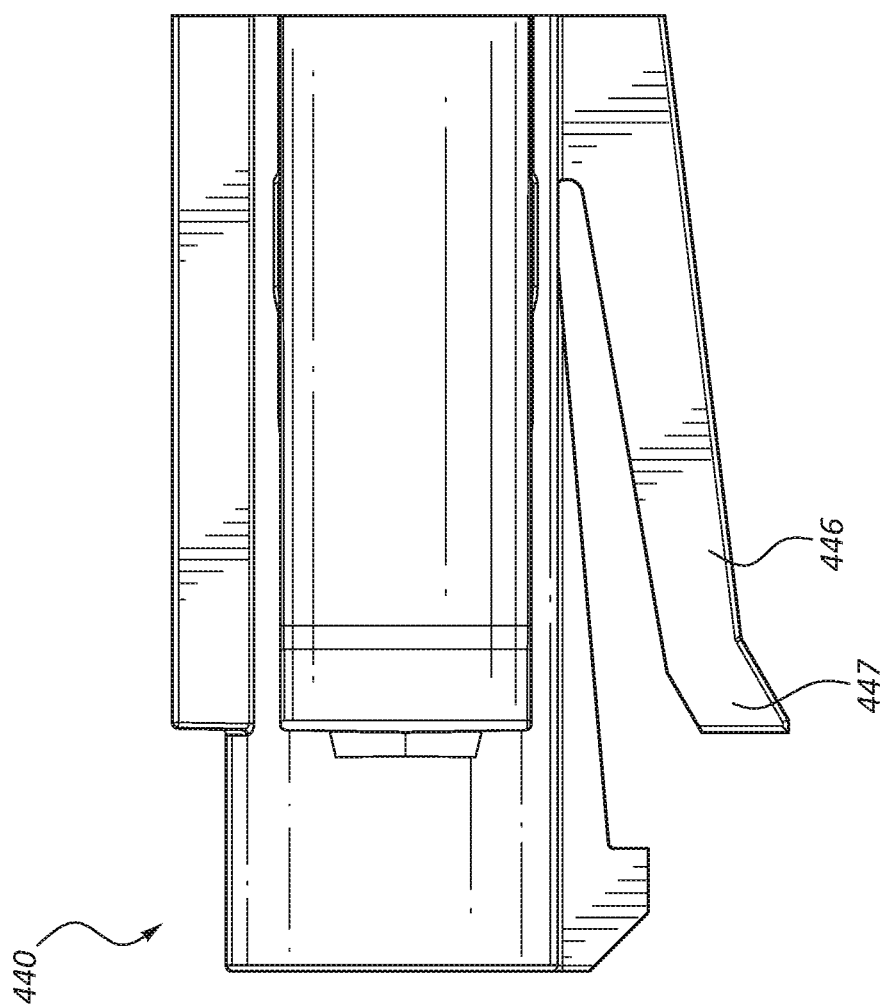
FIG. 17 is a side view of a carrier component of the deployment device of FIGS. 14 and 15.

FIG. 17 is a side view of the carrier 440 of the deployment device 400 of FIGS. 14 and 15. As shown in FIG. 17, the ratchet slide engaging arm 446 extends radially away from a longitudinal axis of the carrier 440. When the carrier 440 is disposed within the handle assembly 402 of FIG. 15, the longitudinal axis of the carrier 440 is disposed along the longitudinal axis of the deployment device 400.

As depicted, the ratchet slide engaging arm 446 comprises an angled portion or "toenail" portion 447 at a distal end of the ratchet slide engaging arm 446. As shown, the angled portion 447 extends radially away from the longitudinal axis of the carrier 440 at a greater angle than the radial extension of the ratchet slide engaging arm 446 in relation to the longitudinal axis of the carrier 440. In some embodiments, the angled portion 447 can enhance engagement between the ratchet slide engaging arm 446 and a given carrier engaging ratchet lug 436 as compared to a ratchet slide engaging arm lacking an angled portion. For example, due at least in part to the semi-continuous disposition of the plurality of the carrier engaging ratchet lugs 436 (as shown in FIGS. 16A and 16B), the angled portion 447 of the ratchet slide engaging arm 446 can allow or permit the ratchet slide engaging arm 446 to deflect radially adjacent to or against at least a portion of the ratchet slide 430 at or adjacent the given carrier engaging ratchet lug 436. The angled portion 447 can provide clearance for the ratchet slide engaging arm 446, allowing the angled portion to engage carrier engaging ratchet lugs 436 (even when closely spaced) without adjacent lugs interfering with the position of the ratchet slide engaging arm 446 and preventing full engagement.

Figure 18:
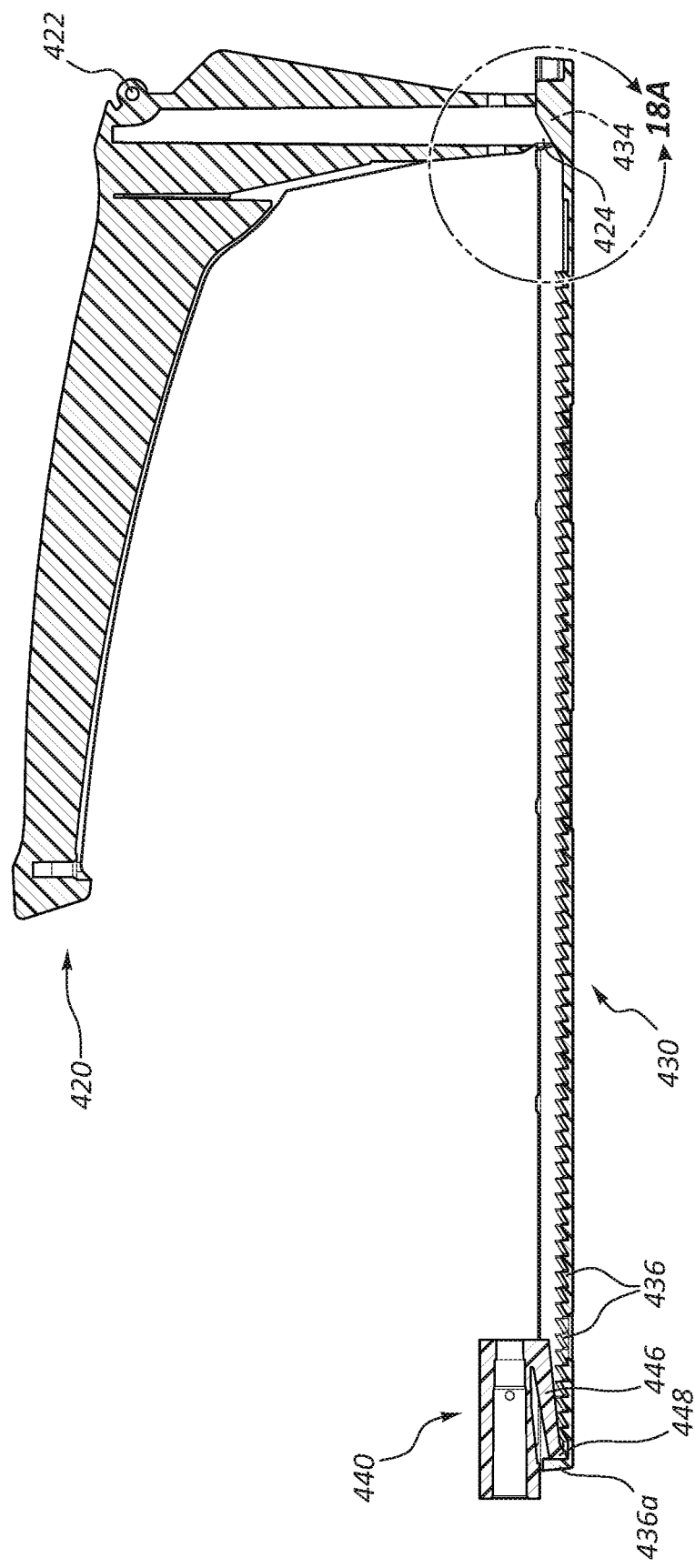
FIG. 18 is a cross-sectional view of another portion of the deployment device shown in FIGS. 14 and 15.
Figure 18A:
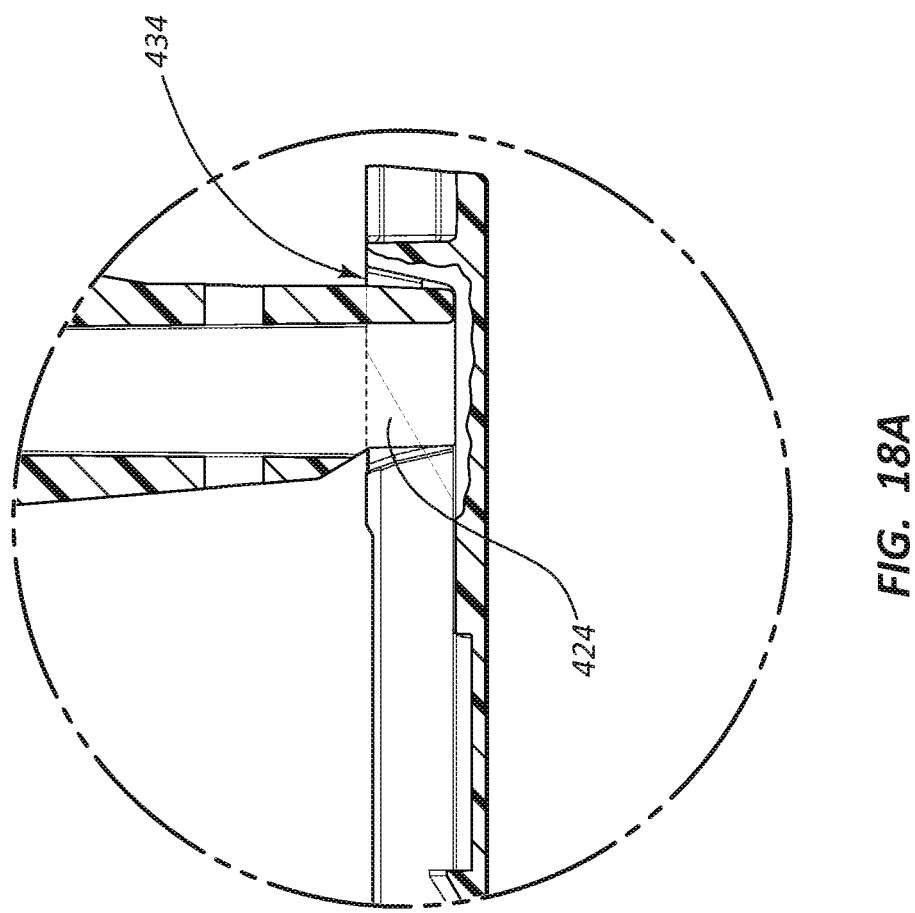
FIG. 18A is a partial cut-away view of a portion of the deployment device shown in FIG. 18.

FIG. 18 is a cross-sectional view of a portion of the deployment device 400 shown in FIGS. 14 and 15. Specifically, the actuator 420, the ratchet slide 430, and the carrier 440 are shown in FIG. 18, in the same relative positions, and along the same cross-sectional plane as in FIG. 15. FIG. 18A is a partial cut-away view of a portion of the cross-sectional view of FIG. 18. As shown, a portion of the ratchet slide 430 has been cut away in this view to show an engagement of the ratchet slide engaging portion 424 with the actuator engaging opening 434.

Referring to FIGS. 15-18A, during depression of the actuator 420 with respect to the housing 410, the actuator 420 rotates around the pin aperture 422. This rotation causes displacement of the ratchet slide engaging portion 424 of the actuator 420. The component of this displacement correlating to proximal displacement of the ratchet slide engaging portion 424 also proximally translates the ratchet slide 430 due to interaction between the ratchet slide engaging portion 424 of the actuator 420 and the actuator engaging opening 434 of the ratchet slide 430. Stated another way, the walls or faces that define the actuator engaging opening 434 may contact the ratchet slide engaging portion 424 such that the ratchet slide 430 is displaced when the actuator 420 is displaced.

Proximal displacement of the ratchet slide 430 also proximally displaces the carrier 440 due to interaction between the carrier engaging ratchet lugs 436 and the ratchet slide engaging arm 446. In the depicted embodiment, a distal surface of the angled portion 447 of the ratchet slide engaging arm 446 is in contact with a proximal face of the distal most carrier engaging ratchet lug 436a. This contact exerts proximal force on the distal surface of the angled portion 447 of the ratchet slide engaging arm 446, displacing the carrier 440 in a proximal direction. Accordingly, the ratchet slide 430 and carrier 440 will move proximally until the actuator 420 reaches the end of the stroke (e.g., either a partial stroke or a full stroke).

Figure 19:
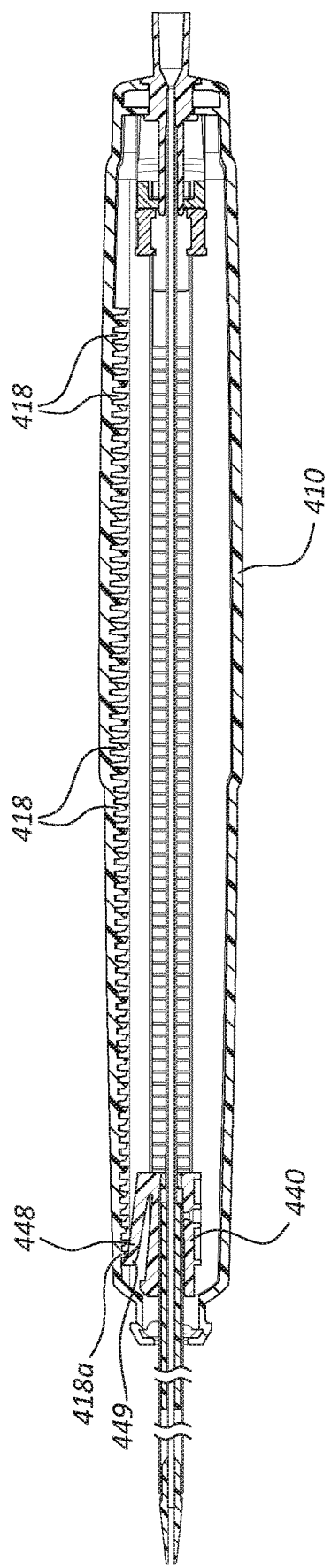
FIG. 19 is a cross-sectional view of yet another portion of the deployment device shown in FIGS. 14 and 15.

FIG. 19 is a cross-sectional view of the housing 410 and the carrier 440 in the same relative positions shown in FIG. 15. The cross-sectional plane of FIG. 19 extends along the longitudinal axis of the deployment device 400; however, the cross-sectional plane of FIG. 19 extends horizontally, orthogonal to the cross-sectional planes of FIGS. 15, 16B, and 18.

As shown in FIG. 19, the carrier 440 comprises a housing engaging arm 448 extending radially away from a longitudinal axis of the carrier 440. The housing 410 comprises a plurality of carrier engaging housing lugs 418. In FIG. 19, exemplary carrier engaging housing lugs are denoted by reference numeral 418, with the distal most carrier engaging housing lug denoted by reference numeral 418a.

As depicted, the housing engaging arm 448 comprises an angled portion or "toenail" portion 449 at a distal end of the housing engaging arm 448. As shown, the angled portion 449 extends radially away from the longitudinal axis of the carrier 440 at a greater angle than the radial extension of the housing engaging arm 448 in relation to the longitudinal axis of the carrier 440. In some embodiments, the angled portion 449 can enhance engagement between the housing engaging arm 448 and a given carrier engaging housing lug 418 as compared to a housing engaging arm lacking an angled portion. For example, due at least in part to the semi-continuous disposition of the plurality of the carrier engaging housing lugs 418, the angled portion 449 of the housing engaging arm 448 can allow or permit the housing engaging arm 448 to deflect radially adjacent to or against at least a portion of the ratchet slide 430 at or adjacent the given carrier engaging housing lug 418. As with the angled portion 447 discussed above, the angled portion 449 can provide clearance for the housing engagement arm 448, allowing the angled portion 449 to engage carrier engaging housing lugs 418 (even when closely spaced) without adjacent lugs interfering with the position of the housing engagement arm 448 and preventing full engagement.

Referring to FIGS. 15-19, as interaction between the actuator 420, ratchet slide 430, and carrier 440 displaces the carrier 440 with respect to the housing 410 (as shown and described above), the housing engaging arm 448 (shown in FIG. 19) of the carrier 440 will deflect radially inward due to contact with one of the carrier engaging housing lugs 418. For example, from the position shown in FIG. 19, as interaction between the distal most carrier engaging ratchet lug 436a and the ratchet slide engaging arm 446 of the carrier 440 draws the carrier 440 proximally, the distal most carrier engaging housing lug 418a causes the housing engaging arm 448 to displace radially inward. The housing engaging arm 448 will continue to deflect radially inward until the distal end of the housing engaging arm 448 is positioned proximal of the distal most carrier engaging housing lug 418a, at which point the housing engaging arm 448 will return to the radially outward configuration shown in FIG. 19. The point at which the housing engaging arm 448 moves proximally of the distal most carrier engaging housing lug 418a may correspond to the stroke of the actuator 420 (e.g., a partial stroke or a full stroke), such that engagement between the housing engaging arm 448 and the next carrier engaging housing lug 418 (moving in a proximal direction) occurs at the end of the stroke. In some embodiments, each carrier engaging housing lug 418 (or at least a portion of each of the carrier engaging housing lugs 418) may be disposed such that a position of the carrier engaging housing lug 418 corresponds to a position of a carrier engaging ratchet lug 436.

Further, a stroke of the actuator 420 can correspond to displacement of the carrier 440 past multiple carrier engaging housing lugs 418. For closely spaced carrier engaging housing lugs 418, the actuator 420 may thus be configured to displace the carrier 440 over a semi-continuous range as the carrier 440 is advanced along the carrier housing engaging lugs 418. Partially depressing the actuator 420 may displace the carrier 440 along and past the carrier engaging housing lugs 418, and upon release of the actuator 420, the carrier 440 may remain engaged with the most-recently passed carrier housing engaging lug 418. Thus, increments of displacement of the carrier 440 may correspond to the spacing the carrier housing engaging lugs 418, rather than the length of the stroke of the actuator 420.

As the actuator 420 is released following the stroke, interaction between the spring 415, the housing 410, and the actuator 420 will return the actuator 420 to the unconstrained position (the position shown in FIG. 15) as discussed above. Corresponding rotation of the actuator 420 about the pin aperture 422 will thus correlate to displacement of the ratchet slide engaging portion 424, including a component of displacement in the distal direction. Interaction between the ratchet slide engaging portion 424 and the actuator engaging opening 434 will then correlate to distal displacement of the ratchet slide 430. Thus, when the actuator 420 is released at the end of a stroke, the actuator 420, the spring 415, and the ratchet slide 430 return to the same positions relative to the housing 410 as shown in FIG. 15.

As the actuator 420 returns to the unconstrained position, however, interaction between the housing engaging arm 448 and the carrier engaging housing lug 418 prevents distal displacement of the carrier 440. Specifically, the distal surface of the angled portion 449 of the housing engaging arm 448 will be in contact with a proximal facing surface of a carrier engaging housing lug 418, the interaction preventing the carrier 440 from returning to the pre-stroke position. In the exemplary stroke discussed above, the distal most carrier engaging housing lug 418a displaced the housing engaging arm 448 during the stroke, and the housing engaging arm 448 engaged with the distal most carrier engaging housing lug 418a following the stroke. Subsequent strokes move the carrier 440 along the plurality of carrier engaging housing lugs 418 in a proximal direction.

As the actuator 420 returns to the unconstrained state, radially inward displacement of the ratchet slide engaging arm 446 of the carrier 440 allows the ratchet slide 430 to move distally with respect to the carrier 440, as engagement between the carrier 440 and the carrier engaging housing lugs 418 arrest distal displacement of the carrier 440.

Referring to FIGS. 15-19, with particular reference to the view of FIG. 18, distal displacement of the ratchet slide 430 with respect to the carrier 440 creates interaction between the carrier engaging ratchet lugs 436 and the angled portion 447 of the ratchet slide engaging arm 446 causing the ratchet slide engaging arm 446 to displace radially inward. The proximal facing surface of the carrier engaging ratchet lugs 436 may be angled to facilitate this interaction. During depression of the actuator 420, engagement between the distal most carrier engaging ratchet lug 436a can displace the carrier 440 in a proximal direction; during the return of the actuator 420, another carrier engaging ratchet lug 436 (in a proximal direction) can cause the radially inward displacement of the ratchet slide engaging arm 446 until the angled portion 447 of the ratchet slide engaging arm 446 is proximal of that carrier engaging ratchet lug 436. At that point the ratchet slide engaging arm 446 returns to a radially outward position (analogous to that shown in FIG. 18) though the distal surface of the angled portion 447 of ratchet slide engaging arm 446 is now engaged with a proximal face of another carrier engaging ratchet lug 436 (again in a proximal direction).

During a full stroke, engagement between a first carrier engaging ratchet lug 436 can displace the carrier 440 in a proximal direction; during the return of the actuator 420, a plurality of the next carrier engaging ratchet lugs 436 (in a proximal direction) can cause a plurality of radially inward displacements of the ratchet slide engaging arm 446 as the angled portion 447 of the ratchet slide engaging arm 446 moves proximally in relation to a plurality of the carrier engaging ratchet lugs 436 during the full stroke. At that point the angled portion 447 of the ratchet slide engaging arm 446 returns to a radially outward position (analogous to that shown in FIG. 18) though the distal surface of the angled portion 447 of ratchet slide engaging arm 446 is now engaged with a proximal face of a second carrier engaging ratchet lug 436 (again in a proximal direction). In such a configuration, a plurality of carrier engaging ratchet lugs 436 may be disposed between the first carrier engaging ratchet lug 436 engaged during the stroke and the second carrier engaging ratchet lug 436 engaged at the end of that same stroke. For example, 1, 2, 3, 4, 5, 6, or more carrier engaging ratchet lugs 436 may be disposed between the first carrier engaging ratchet lug 436 engaged during a single stroke and the second carrier engaging ratchet lug 436 engaged at the end of that single stroke.

Displacement of the ratchet slide 430 sufficient to move to engagement with a subsequent carrier engaging ratchet lug 436 may correspond with the magnitude of ratchet slide 430 displacement corresponding to a return of the actuator 420. One return of the actuator 420 following at least a partial stroke can move the ratchet slide 430 such that a plurality of carrier engaging ratchet lugs 436 may serially engage the carrier 440 during the stroke.

Accordingly, as described above, depressing the actuator 420 for a full stroke, then allowing the actuator 420 to return to the unconstrained position, displaces the carrier 440 with respect to the housing 410 in discrete increments, corresponding to the distance between a plurality of carrier engaging housing lugs 418 along the longitudinal direction. Depressing the actuator 420 for a partial stroke, then allowing the actuator 420 to return to the unconstrained position, can displace the carrier 440 with respect to the housing 410 in discrete increments, corresponding to the distance between adjacent carrier engaging housing lugs 418 along the longitudinal direction.

As detailed below, the relative position of the carrier 440 with respect to the housing 410 may correlate to the degree of deployment of a stent from the deployment device 400. Thus, visual, audible, and tactile feedback as to the position of the carrier 440 provides a user with information regarding stent deployment during use of the deployment device 400. This information may correlate to increased control during deployment as the practitioner quickly and intuitively can surmise the degree of stent deployment.

In some configurations, at least a portion of the elongate delivery catheter assembly 404 may lengthen and/or stretch during use of the deployment device 400. The configuration of the deployment device 400 (e.g., comprising the semi-continuous disposition of the plurality of the carrier engaging ratchet lugs 436) can allow or permit more than one increment of displacement of the carrier 440 in relation to the ratchet slide 430. Furthermore, the configuration of the deployment device 400 can allow or permit finely tuned deployment of the stent. For example, the stent can be deployed in about a 1 mm increment, about a 2 mm increment, about a 3 mm increment, about a 4 mm increment, about a 5 mm increment, or any other suitable increment.

The increments of displacement of the carrier 440 may be about 0.5 mm, about 1 mm, about 2 mm, about 3 mm, about 4 mm, about 5 mm, about 10 mm, about 25 mm, about 50 mm, about 100 mm, or any other suitable increment of displacement. The incremental displacement of the carrier 440 may further facilitate partial deployment of a stent, allowing a practitioner to deploy the stent in increments, potential adjusting or confirming the position of the stent between these increments Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art, and having the benefit of this disclosure, that changes may be made to the details of the above-described embodiments without departing from the underlying principles of the disclosure herein.

The invention claimed is:

1. A method of adjusting an effective length of a stent during deployment of the stent, comprising:
   deploying a first portion of the stent from a stent deployment device, wherein the first portion is engaged with a vessel;
   deploying a second portion of the stent from the stent deployment device, wherein the stent comprises a plurality of rows of helical coils that are nestable with each other such that each row of the plurality of rows of helical coils is configured to be displaced toward at least a portion of an adjacent row; and nesting and unnesting adjacent rows of helical coils in the first portion and the second portion of the stent to change the effective length of the stent while deploying the first portion and the second portion of the stent;

wherein bends of the plurality of rows of helical coils circumferentially align with each other along an axis parallel to a longitudinal axis of the stent.

2. The method of claim 1, wherein a length of the second portion is compressed.

3. The method of claim 1, wherein a length of the second portion is stretched.

4. The method of claim 1, wherein the first portion comprises a first plurality of rows of helical coils, and wherein the second portion comprises a second plurality of rows of helical coils.

5. The method of claim 4, wherein a first distance between each row of the first plurality of rows of helical coils is greater than a second distance between each row of the second plurality of rows of helical coils after the stent is deployed.

6. The method of claim 4, wherein a first distance between each row of helical coils of the deployed first plurality of rows of helical coils is less than a second distance between each row of helical coils of the deployed second plurality of rows of helical coils.

7. The method of claim 1, further comprising supporting a non-deployed portion of the stent with a pliant member, wherein the non-deployed portion of the stent is imprinted on the pliant member so that the pliant member supports the plurality of rows of helical coils.

8. The method of claim 1, further comprising incrementally deploying the stent.

9. The method of claim 8, wherein incrementally deploying the stent comprises retracting an outer sheath incrementally.

10. The method of claim 1, further comprising displacing the stent deployment device by distally displacing the stent deployment device with respect to the first portion.

11. The method of claim 1, further comprising displacing the stent deployment device by proximally displacing the stent deployment device with respect to the first portion.

12. A method of treating a vascular lesion, comprising:
positioning a stent adjacent the vascular lesion, wherein the stent is constrained by an outer sheath of a stent deployment device;
actuating the stent deployment device, wherein the outer sheath is retracted relative to the stent;
deploying a distal portion of the stent against a vessel wall adjacent the vascular lesion, such that the distal portion is not constrained by the outer sheath;
deploying a middle portion of the stent against the vessel wall, such that the middle portion is not constrained by the outer sheath;
displacing the stent deployment device relative to the deployed distal portion to change an effective length of the stent;
deploying a proximal portion of the stent;
applying a radial outwardly directed force to the vessel wall adjacent the vascular lesion by the stent,
wherein the stent comprises a plurality of rows of helical coils that are nestable with each other such that each row of the plurality of rows of helical coils is configured to be displaced toward at least a portion of an adjacent row; and
nesting and unnesting adjacent rows of helical coils in the distal portion, middle portion, and the proximal portion of the stent to change the effective length of the stent while deploying the distal portion, the middle portion, and the proximal portion of the stent;
wherein bends of the plurality of rows of helical coils circumferentially align with each other along an axis parallel to a longitudinal axis of the stent.

13. The method of claim 12, wherein displacing the stent deployment device relative to the deployed distal portion comprises distally displacing the stent deployment device, such that the deployed middle portion is compressed.

14. The method of claim 12, wherein displacing the stent deployment device relative to the deployed distal portion comprises proximally displacing the stent deployment device, such that the deployed middle portion is stretched.

15. The method of claim 12, further comprising supporting a non-deployed portion of the stent with a pliant member, wherein the non-deployed portion of the stent is imprinted on the pliant member so that the pliant member supports the plurality of rows of helical coils.

16. The method of claim 12, wherein the plurality of rows of helical coils are nestable with each other such that each row of the plurality of rows of helical coils is configured to be disposed around at least a portion of an outer surface of an adjacent row.

17. A method of adjusting a length of a stent to fit an anatomical feature, comprising:
positioning the stent adjacent the anatomical feature;
deploying a first portion of the stent from a stent deployment device;
deploying a second portion of the stent from the stent deployment device,
wherein the stent comprises a plurality of rows of helical coils that are nestable with each other such that each row of the plurality of rows of helical coils is configured to be displaced toward at least a portion of an adjacent row; and
nesting and unnesting adjacent rows of helical coils in the first portion and in the second portion to change an effective length of the stent while deploying the first portion and the second portion of the stent;
wherein bends of the plurality of rows of helical coils circumferentially align with each other along an axis parallel to a longitudinal axis of the stent.

18. The method of claim 17, further comprising displacing the stent deployment device relative to the deployed first portion by distally displacing the stent deployment device, such that second portion is compressed.

19. The method of claim 17, further comprising displacing the stent deployment device relative to the deployed first portion by proximally displacing the stent deployment device, such that the second portion is stretched.

20. The method of claim 17, wherein the anatomical feature is one or more of a branch vessel, a vessel stricture, and a vessel lesion.

* * * * *